United States Patent
Ewer et al.

(10) Patent No.: US 10,149,702 B2
(45) Date of Patent: Dec. 11, 2018

(54) POLYAXIAL SCREW AND ROD SYSTEM

(71) Applicant: IMDS LLC, Providence, UT (US)

(72) Inventors: Darin Ewer, Providence, UT (US); Kyle Atwood, Paradise, UT (US)

(73) Assignee: IMDS LLC, Providence, UT (US)

( * ) Notice: Subject to any disclaimer, the term of this patent is extended or adjusted under 35 U.S.C. 154(b) by 68 days.

(21) Appl. No.: 14/993,888

(22) Filed: Jan. 12, 2016

(65) Prior Publication Data
US 2016/0199104 A1    Jul. 14, 2016

Related U.S. Application Data

(60) Provisional application No. 62/102,578, filed on Jan. 12, 2015.

(51) Int. Cl.
*A61B 17/70* (2006.01)

(52) U.S. Cl.
CPC ................. *A61B 17/7038* (2013.01)

(58) Field of Classification Search
CPC ............ A61B 17/7035; A61B 17/7038; A61B 17/7046
See application file for complete search history.

(56) References Cited

U.S. PATENT DOCUMENTS

| | | |
|---|---|---|
| 5,520,690 A | 5/1996 | Errico |
| 5,531,746 A | 7/1996 | Errico |
| 5,607,426 A | 3/1997 | Ralph |
| 5,643,265 A | 7/1997 | Errico |
| 5,647,873 A | 7/1997 | Errico |
| 5,669,911 A | 9/1997 | Errico |
| 5,690,630 A | 11/1997 | Errico |
| 5,725,588 A | 3/1998 | Errico |
| 5,782,833 A | 7/1998 | Haider |
| 5,817,094 A | 10/1998 | Errico |
| 5,876,402 A | 3/1999 | Errico |
| 5,882,350 A | 3/1999 | Ralph |
| 5,888,204 A | 3/1999 | Ralph |
| 5,910,142 A | 6/1999 | Tatar |
| 6,113,601 A * | 9/2000 | Tatar .................. A61B 17/7037 606/266 |
| RE37,665 E | 4/2002 | Ralph |
| 6,402,752 B2 | 6/2002 | Schäffler Wachter |
| 6,485,494 B1 | 11/2002 | Haider |
| 6,520,963 B1 | 2/2003 | McKinley |
| 6,540,748 B2 | 4/2003 | Lombardo |
| 6,554,834 B1 | 4/2003 | Crozet |
| 6,558,387 B2 | 5/2003 | Errico |
| 6,565,567 B1 | 5/2003 | Haider |
| 6,626,908 B2 | 9/2003 | Cooper |
| 6,660,005 B2 | 12/2003 | Toyama |
| 6,780,186 B2 | 8/2004 | Errico |
| 6,835,196 B2 | 12/2004 | Biedermann |
| 6,896,677 B1 | 5/2005 | Lin |
| 6,974,460 B2 | 12/2005 | Carbone |
| RE39,089 E | 5/2006 | Ralph |

(Continued)

*Primary Examiner* — Jacqueline Johanas
(74) *Attorney, Agent, or Firm* — Maywood IP Law; G. Jo Hays; David W. Meibos

(57) ABSTRACT

Screw and rod systems include polyaxial and hinge joints which provide independent first and second ranges of motion. The first and second ranges of motion are additive in a direction along the rod, so that the screw has greater angulation relative to the rod along the rod than transverse to the rod.

20 Claims, 24 Drawing Sheets

(56) References Cited

U.S. PATENT DOCUMENTS

| | | |
|---|---|---|
| 7,087,057 B2 | 8/2006 | Konieczynski |
| 7,211,086 B2 | 5/2007 | Biedermann |
| 7,335,202 B2 | 2/2008 | Matthis |
| 7,377,923 B2 | 5/2008 | Purcell |
| 7,503,918 B2 | 3/2009 | Baccelli |
| 7,503,924 B2 | 3/2009 | Lee |
| 7,621,957 B2 | 11/2009 | Errico |
| 7,635,380 B2 | 12/2009 | Zucherman |
| 7,678,139 B2 | 3/2010 | Garamszegi |
| 7,682,377 B2 | 3/2010 | Konieczynski |
| 7,722,651 B2 | 5/2010 | Kwak |
| 7,857,834 B2 | 12/2010 | Boschert |
| 7,867,257 B2 | 1/2011 | Na |
| 7,909,855 B2 | 3/2011 | Drewry |
| 7,927,359 B2 | 4/2011 | Trautwein |
| 7,942,900 B2 | 5/2011 | Winslow |
| 7,942,909 B2 | 5/2011 | Hammill, Sr. |
| 7,942,910 B2 | 5/2011 | Doubler |
| 7,942,911 B2 | 5/2011 | Doubler |
| 7,947,065 B2 | 5/2011 | Hammill, Sr. |
| 7,951,173 B2 | 5/2011 | Hammill, Sr. |
| 7,951,174 B2 | 5/2011 | Kwak |
| 7,963,978 B2 | 6/2011 | Winslow |
| 7,967,849 B2 | 6/2011 | Carson |
| RE42,545 E | 7/2011 | Ralph |
| 7,985,243 B2 | 7/2011 | Winslow |
| 7,993,372 B2 | 8/2011 | Winslow |
| 8,002,800 B2 | 8/2011 | Winslow |
| 8,002,803 B2 | 8/2011 | Winslow |
| 8,007,518 B2 | 8/2011 | Winslow |
| 8,012,175 B2 | 9/2011 | Winslow |
| 8,012,181 B2 | 9/2011 | Winslow |
| 8,016,861 B2 | 9/2011 | Mitchell |
| 8,021,396 B2 | 9/2011 | Winslow |
| 8,034,086 B2 | 10/2011 | Iott |
| 8,048,112 B2 | 11/2011 | Suzuki |
| 8,048,113 B2 | 11/2011 | Winslow |
| 8,048,115 B2 | 11/2011 | Winslow |
| 8,048,121 B2 | 11/2011 | Mitchell |
| 8,048,122 B2 | 11/2011 | Mitchell |
| 8,048,123 B2 | 11/2011 | Mitchell |
| 8,048,125 B2 | 11/2011 | Mitchell |
| 8,048,128 B2 | 11/2011 | Klyce |
| 8,052,721 B2 | 11/2011 | Winslow |
| 8,052,722 B2 | 11/2011 | Winslow |
| 8,057,514 B2 | 11/2011 | Winslow |
| 8,057,515 B2 | 11/2011 | Flynn |
| 8,057,517 B2 | 11/2011 | Flynn |
| 8,066,744 B2 | 11/2011 | Justis |
| 8,066,747 B2 | 11/2011 | Zucherman |
| 8,070,774 B2 | 12/2011 | Winslow |
| 8,070,775 B2 | 12/2011 | Winslow |
| 8,070,776 B2 | 12/2011 | Winslow |
| 8,070,780 B2 | 12/2011 | Zucherman |
| 8,075,603 B2 | 12/2011 | Hammill, Sr. |
| 8,080,039 B2 | 12/2011 | Zucherman |
| 8,083,772 B2 | 12/2011 | Winslow |
| 8,083,775 B2 | 12/2011 | Winslow |
| 8,092,501 B2 | 1/2012 | Mitchell |
| 8,097,024 B2 | 1/2012 | Winslow |
| 8,100,946 B2 | 1/2012 | Strausbaugh |
| 8,105,356 B2 | 1/2012 | Zucherman |
| 8,105,359 B2 | 1/2012 | Winslow |
| 8,109,970 B2 | 2/2012 | Winslow |
| 8,114,130 B2 | 2/2012 | Winslow |
| 8,114,134 B2 | 2/2012 | Winslow |
| 8,118,842 B2 | 2/2012 | Klyce |
| 8,133,262 B2 | 3/2012 | Whipple |
| 8,137,387 B2 | 3/2012 | Garamszegi |
| 8,142,480 B2 | 3/2012 | Cain |
| 8,147,520 B2 | 4/2012 | Cain |
| 8,162,987 B2 | 4/2012 | Zucherman |
| 8,162,990 B2 | 4/2012 | Potash |
| 8,167,912 B2 | 5/2012 | Jacofsky |
| 8,172,881 B2 | 5/2012 | Cain |
| 8,177,815 B2 | 5/2012 | Cain |
| 8,182,515 B2 | 5/2012 | Cain |
| 8,182,516 B2 | 5/2012 | Winslow |
| 8,192,469 B2 | 6/2012 | Cain |
| 8,197,518 B2 | 6/2012 | Hammill, Sr. |
| 8,211,150 B2 | 7/2012 | Cain |
| 8,211,155 B2 | 7/2012 | Winslow |
| 8,216,281 B2 | 7/2012 | Winslow |
| 8,221,472 B2 | 7/2012 | Peterson |
| 8,257,397 B2 | 9/2012 | Winslow |
| 8,257,401 B2 | 9/2012 | Cermak |
| 8,267,979 B2 | 9/2012 | Flynn |
| 8,273,112 B2 | 9/2012 | Garamszegi |
| 8,277,490 B2 | 10/2012 | Freeman |
| 8,298,267 B2 | 10/2012 | Mitchell |
| 8,313,516 B2 | 11/2012 | Konieczynski |
| 8,317,836 B2 | 11/2012 | Zucherman |
| 8,333,792 B2 | 12/2012 | Winslow |
| 8,337,530 B2 | 12/2012 | Hestad |
| 8,337,536 B2 | 12/2012 | Mitchell |
| 8,372,122 B2 | 2/2013 | Winslow |
| 8,394,127 B2 | 3/2013 | Winslow |
| 8,414,622 B2 | 4/2013 | Potash |
| 8,430,914 B2 | 4/2013 | Spratt |
| 8,430,917 B2 | 4/2013 | Rezach |
| 8,449,577 B2 | 5/2013 | Kloss |
| 8,449,578 B2 | 5/2013 | Keiser |
| 8,465,530 B2 | 6/2013 | Hammill, Sr. |
| 8,470,001 B2 | 6/2013 | Trautwein |
| 8,475,495 B2 | 7/2013 | Iott |
| 8,475,500 B2 | 7/2013 | Potash |
| 8,480,711 B2 | 7/2013 | Garamszegi |
| 8,491,641 B2 | 7/2013 | Nihalani |
| 8,506,601 B2 | 8/2013 | Gephart |
| 8,568,451 B2 | 10/2013 | Zucherman |
| 8,603,144 B2 | 12/2013 | Kwak |
| 8,617,216 B2 | 12/2013 | Brumfield |
| 8,617,217 B2 | 12/2013 | Iott |
| 8,641,737 B2 | 2/2014 | Matthis |
| 8,663,288 B2 | 3/2014 | Konieczynski |
| 8,679,162 B2 | 3/2014 | Strausbaugh |
| 8,685,064 B2 | 4/2014 | Hestad |
| 8,696,717 B2 | 4/2014 | Rock |
| 8,740,946 B2 | 6/2014 | Peterson |
| 8,790,374 B2 | 7/2014 | Iott |
| 8,808,330 B2 | 8/2014 | Biedermann |
| 8,814,919 B2 | 8/2014 | Barrus |
| 8,845,700 B2 | 9/2014 | Kwak |
| 8,852,239 B2 | 10/2014 | Jackson |
| 9,763,701 B2 * | 9/2017 | Shaffrey ............ A61B 17/7032 |
| 2005/0080415 A1 | 4/2005 | Keyer |
| 2005/0154391 A1 | 7/2005 | Doherty |
| 2005/0171542 A1 | 8/2005 | Biedermann |
| 2005/0187548 A1 | 8/2005 | Butler |
| 2005/0192571 A1 | 9/2005 | Abdelgany |
| 2005/0203515 A1 | 9/2005 | Doherty |
| 2006/0200131 A1 | 9/2006 | Chao |
| 2006/0229615 A1 * | 10/2006 | Abdou ............... A61B 17/7035 |
| | | 606/256 |
| 2006/0264933 A1 | 11/2006 | Baker |
| 2006/0276792 A1 | 12/2006 | Ensign |
| 2007/0043355 A1 * | 2/2007 | Bette ................. A61B 17/7037 |
| | | 606/250 |
| 2007/0161999 A1 | 7/2007 | Biedermann |
| 2008/0021473 A1 | 1/2008 | Butler |
| 2008/0140135 A1 | 6/2008 | Konieczynski |
| 2008/0167689 A1 | 7/2008 | Matthis |
| 2008/0262556 A1 | 10/2008 | Jacofsky |
| 2010/0030224 A1 | 2/2010 | Winslow |
| 2010/0036437 A1 | 2/2010 | Mitchell |
| 2010/0331889 A1 * | 12/2010 | Abdou ............... A61B 17/7035 |
| | | 606/264 |
| 2011/0015677 A1 | 1/2011 | Biedermann |
| 2011/0230917 A1 | 9/2011 | Carson |
| 2011/0257687 A1 * | 10/2011 | Trieu ................. A61B 17/7001 |
| | | 606/267 |
| 2012/0016425 A1 | 1/2012 | Shaffrey |
| 2012/0046696 A1 | 2/2012 | Winslow |
| 2012/0046699 A1 | 2/2012 | Jones |

(56) References Cited

U.S. PATENT DOCUMENTS

| | | | |
|---|---|---|---|
| 2012/0109219 A1 | 5/2012 | Matthis | |
| 2012/0123478 A1 | 5/2012 | Winslow | |
| 2012/0143257 A1 | 6/2012 | Winslow | |
| 2012/0143258 A1 | 6/2012 | Winslow | |
| 2012/0203280 A1 | 8/2012 | Winslow | |
| 2012/0209335 A1 | 8/2012 | Termyna | |
| 2012/0221055 A1* | 8/2012 | Copf | A61B 17/7041 606/264 |
| 2012/0296380 A1* | 11/2012 | Simonson | A61B 17/7038 606/278 |
| 2012/0303073 A1 | 11/2012 | Cermak | |
| 2012/0330364 A1 | 12/2012 | Jacofsky | |
| 2013/0046345 A1 | 2/2013 | Jones | |
| 2013/0079830 A1 | 3/2013 | Garamszegi | |
| 2013/0090693 A1 | 4/2013 | Strausbaugh | |
| 2013/0184770 A1 | 7/2013 | Buttermann | |
| 2013/0268006 A1 | 10/2013 | Garamszegi | |
| 2013/0289623 A1 | 10/2013 | Potash | |
| 2014/0058451 A1 | 2/2014 | Iott | |
| 2014/0058452 A1 | 2/2014 | Iott | |
| 2014/0114358 A1 | 4/2014 | Brumfield | |
| 2014/0142640 A1 | 5/2014 | Hestad | |
| 2014/0172018 A1 | 6/2014 | Gephart | |
| 2014/0180346 A1* | 6/2014 | Abdou | A61B 17/7035 606/305 |
| 2014/0180347 A1 | 6/2014 | Konieczynski | |
| 2014/0188172 A1 | 7/2014 | Nichols | |
| 2014/0222079 A1 | 8/2014 | Matthis | |
| 2014/0222089 A1 | 8/2014 | Iott | |
| 2014/0249582 A1 | 9/2014 | Strausbaugh | |
| 2014/0249590 A1 | 9/2014 | Peterson | |
| 2014/0277172 A1* | 9/2014 | Abdou | A61B 17/7035 606/279 |
| 2016/0199104 A1* | 7/2016 | Ewer | A61B 17/7038 606/266 |

* cited by examiner

POLYAXIAL SCREW AND ROD SYSTEM

CROSS-REFERENCE TO RELATED APPLICATIONS

The present application claims the benefit of:

U.S. Provisional Application Ser. No. 62/102,578, entitled POLYAXIAL SCREW AND ROD SYSTEM, which was filed on Jan. 12, 2015.

The foregoing is incorporated by reference as though set forth herein in its entirety.

BACKGROUND

This disclosure relates to the field of spinal fixation with screws and rods. While this type of fixation is frequently applied to the posterior aspect of the spine, there are times when screw and rod fixation may be applied to the lateral or anterior aspects of the spine. Fixation may include vertebrae, and may extend to the skull and/or the sacrum. Screw and rod fixation may be applied to the spine by securing screws in the spinal pedicles, vertebral bodies, sacrum, occiput, and so forth. Screw and rod fixation may also be applied to the rest of the skeleton.

This disclosure presents several examples of screw and rod systems, each of which provides at least two independent joints for angular movement between the central longitudinal axis of the screw and the central longitudinal axis of the rod. These examples may provide more angulation, or range of motion, than designs which incorporate only one joint. These examples may provide more than 50 degrees of angulation (half angle) at any rotational position of the screw relative to the rod, or in a preferred orientation of the screw relative to the rod. The joints disclosed herein may be hinge joints which permit rotation about an axis, ball and socket joints which permit multidirectional or polyaxial rotation about a point, or other types of joints or modifications thereof.

SUMMARY

The various systems and methods of the present technology have been developed in response to the present state of the art, and in particular, in response to the problems and needs in the art that have not yet been fully solved by currently available screw and rod systems for spinal fixation. The systems and methods of the present technology may provide multiple joints so that the screw can be angled quite close to the rod.

In an aspect of the technology, a screw and rod system includes: a screw with a spherical head, a shaft extending from the spherical head, and a central longitudinal screw axis extending along the shaft; a rod with a central longitudinal rod axis extending along the rod; and a tulip sub-assembly including a carrier and a body, wherein the carrier includes a carrier socket that receives the spherical head of the screw, wherein the body includes a slot that receives the rod; wherein the carrier forms a hinge joint with the body so that the carrier has a first range of motion relative to the body about a hinge axis, wherein, when the slot of the body receives the rod, the hinge axis is transverse to the rod; wherein the spherical head of the screw forms a ball and socket joint with the carrier socket so that the screw has a second range of motion relative to the carrier about a pivot point centered in the spherical head of the screw, wherein the second range of motion is a cone.

Embodiments of the system may include some or all of the following attributes. The first range of motion has an included angle of at least 35 degrees and the second range of motion has an included angle of at least 55 degrees. The pivot point lies on the hinge axis. The tulip sub-assembly includes the screw and a lower saddle component, wherein the lower saddle component includes a saddle socket that receives the spherical head of the screw, wherein the spherical head of the screw forms a joint with the saddle socket. A socket of the body receives a portion of the lower saddle component, wherein the lower saddle component is free to translate along the socket of the body, wherein the lower saddle component is prevented from rotating relative to the body. A groove of the lower saddle component receives the rod, wherein the groove is opposite the saddle socket. The tulip sub-assembly includes a locking element that engages the body to apply a compressive force against the rod, the lower saddle, and the screw within the carrier.

In another aspect of the technology, a screw and rod system including: a screw with a spherical head, a shaft extending from the spherical head, and a central longitudinal screw axis extending along the shaft; and a rod with a central longitudinal rod axis extending along the rod; wherein the screw has a first range of motion relative to the rod about a hinge axis, wherein the hinge axis is transverse to the rod axis; wherein the screw has a second range of motion relative to the rod about a pivot point centered in the spherical head, wherein the second range of motion is a cone; wherein the first and second ranges of motion are additive about the hinge axis so that the screw has an effective range of motion about the hinge axis that is greater than the second range of motion.

Embodiments of the system may include some or all of the following attributes. The first range of motion has an included angle of at least 35 degrees, the second range of motion has an included angle of at least 55 degrees, and the effective range of motion has an included angle of at least 90 degrees. The pivot point lies on the hinge axis. The system includes a carrier coupled by a first ball and socket joint to the spherical head of the screw, wherein the first ball and socket joint rotates about the pivot point, wherein the carrier is coupled by a hinge joint to a body component, wherein the hinge joint rotates about the hinge axis, wherein the body component includes a slot that receives the rod. The system includes a lower saddle component coupled by a second ball and socket joint to the spherical head of the screw, wherein the second ball and socket joint rotates about the pivot point, wherein the lower saddle component includes a groove that receives the rod, wherein the groove is opposite the second ball and socket joint. A cylindrical portion of the lower saddle component is received in a cylindrical socket of the body component, wherein the lower saddle component is free to translate along the cylindrical socket of the body component, wherein the lower saddle component is prevented from rotating within the cylindrical socket of the body component. The system includes a locking element that engages the body component to apply a compressive force against the rod, the lower saddle component, and the screw within the carrier.

In another aspect of the technology, a screw and rod system including: a screw with a spherical head, a shaft extending from the spherical head, a pivot point centered in the spherical head, and a central longitudinal screw axis extending along the shaft; and a rod with a central longitudinal rod axis extending along the rod; wherein the screw has a first range of motion relative to the rod about a hinge axis, wherein the hinge axis is transverse to the rod axis;

wherein the screw has a second range of motion relative to the rod about a pivot point centered in the spherical head, wherein the second range of motion is a cone; wherein the second range of motion is independent of the first range of motion.

Embodiments of the system may include some or all of the following attributes. The first range of motion has an included angle of at least 35 degrees and the second range of motion has an included angle of at least 55 degrees. The pivot point lies on the hinge axis. The system includes a carrier coupled by a first ball and socket joint to the spherical head of the screw, wherein the first ball and socket joint rotates about the pivot point, wherein the carrier is coupled by a hinge joint to a body component, wherein the hinge joint rotates about the hinge axis, wherein the body component includes a slot that receives the rod. The system includes a lower saddle component coupled by a second ball and socket joint to the spherical head of the screw, wherein the second ball and socket joint rotates about the pivot point, wherein the lower saddle component includes a groove that receives the rod, wherein the groove is opposite the second ball and socket joint, wherein a cylindrical portion of the lower saddle component is received in a socket of the body component, wherein the lower saddle component is free to translate along the socket of the body component, wherein the lower saddle component is prevented from rotating within the socket of the body component. The system includes a locking element that engages the body component to apply a compressive force against the rod, the lower saddle component, and the screw within the carrier.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

DETAILED DESCRIPTION

The technology disclosed herein will be best understood by reference to the drawings, wherein like parts are designated by like numerals throughout. It will be readily understood that the components, as generally described and illustrated in the figures herein, could be arranged and designed in a wide variety of different configurations. Thus, the following more detailed description of the apparatus, systems, and method is not intended to limit the scope of the invention, as claimed in this or any other application claiming priority to this application, but is merely representative of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

This disclosure relates to the field of spinal fixation with screws and rods. While this type of fixation is frequently applied to the posterior aspect of the spine, there are times when screw and rod fixation may be applied to the lateral or anterior aspects of the spine. Screw and rod fixation may be applied to the spine by securing screws in the spinal pedicles, vertebral bodies, sacrum, and so forth. Screw and rod fixation may also be applied to the rest of the skeleton.

This disclosure presents several examples of screw and rod systems, each of which provides at least two independent joints for angular movement between the axis of the screw and the axis of the rod. These examples may provide more angulation than designs which incorporate only one joint. These examples may provide more than 50 degrees of angulation at any rotational position of the screw. The joints disclosed herein may be hinge joints which permit rotation about an axis, ball and socket joints which permit multidirectional or polyaxial rotation about a point, or other types of joints or modifications thereof.

Figure 1:
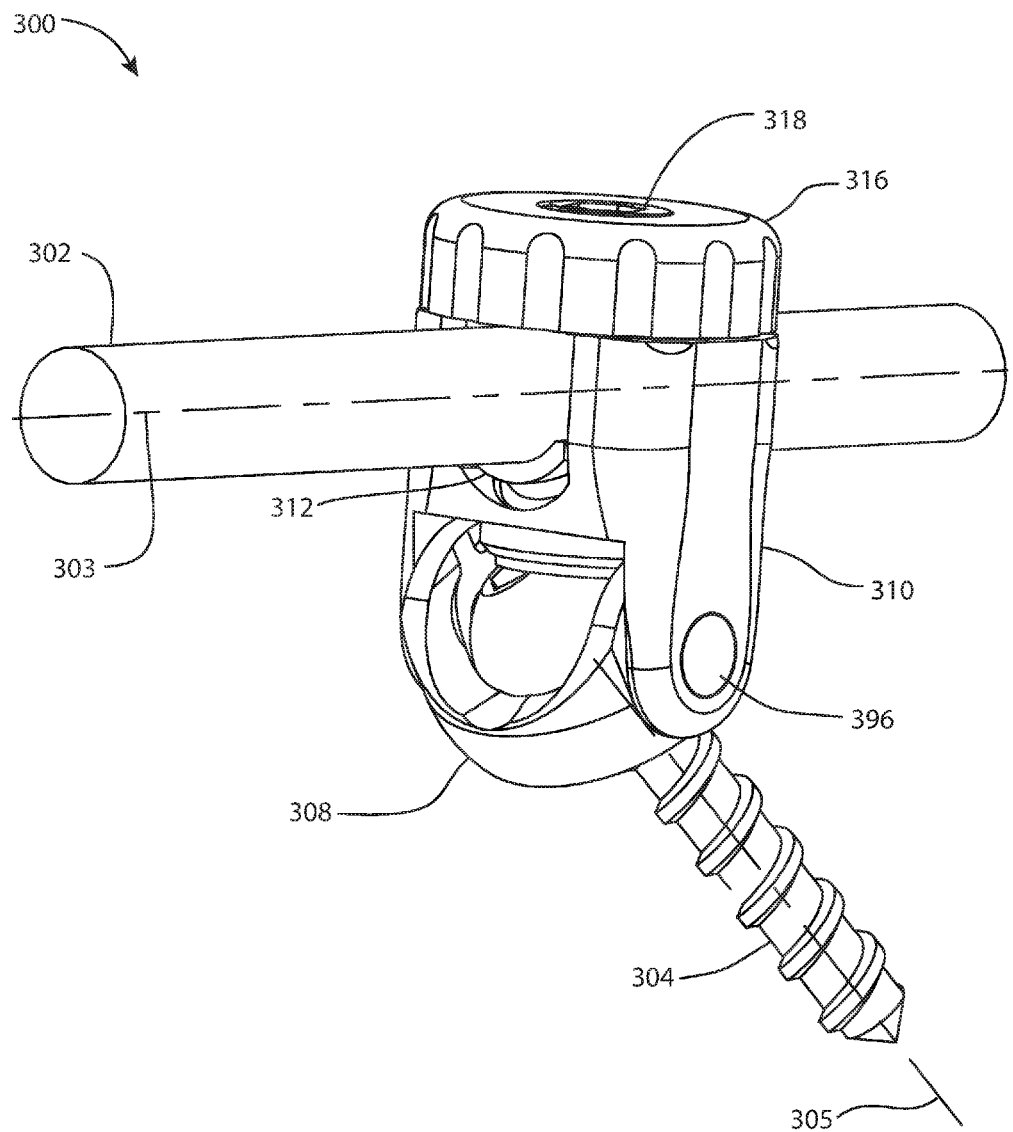
FIG. 1 is an oblique view of a screw and rod system.
Figure 2:
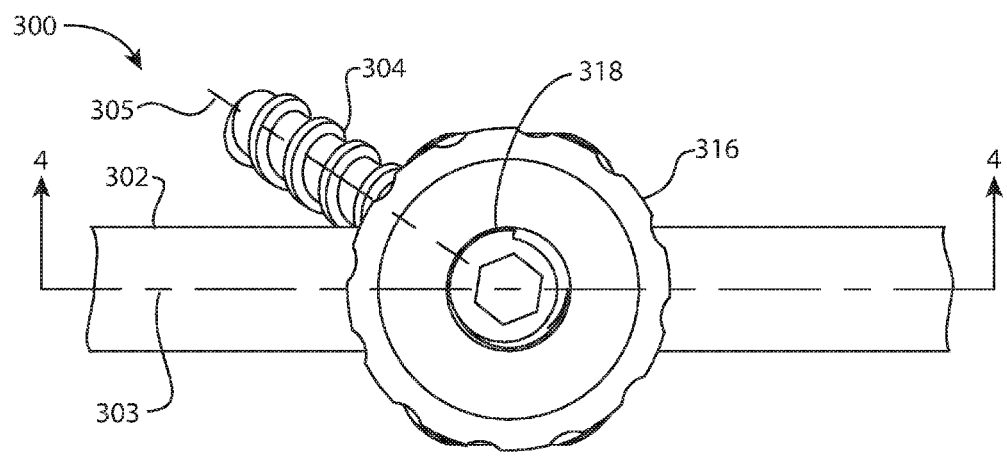
FIG. 2 is a top view of the screw and rod system of FIG. 1.
Figure 3:
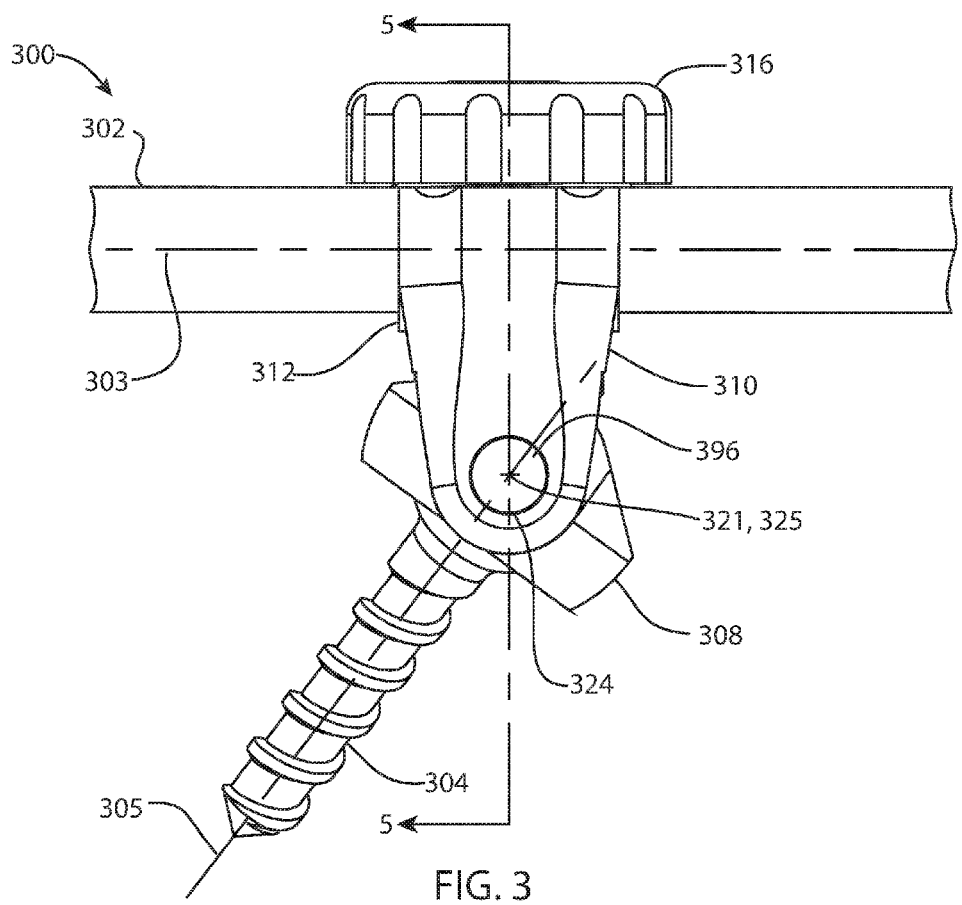
FIG. 3 is a front view of the screw and rod system of FIG. 1.
Figure 4:
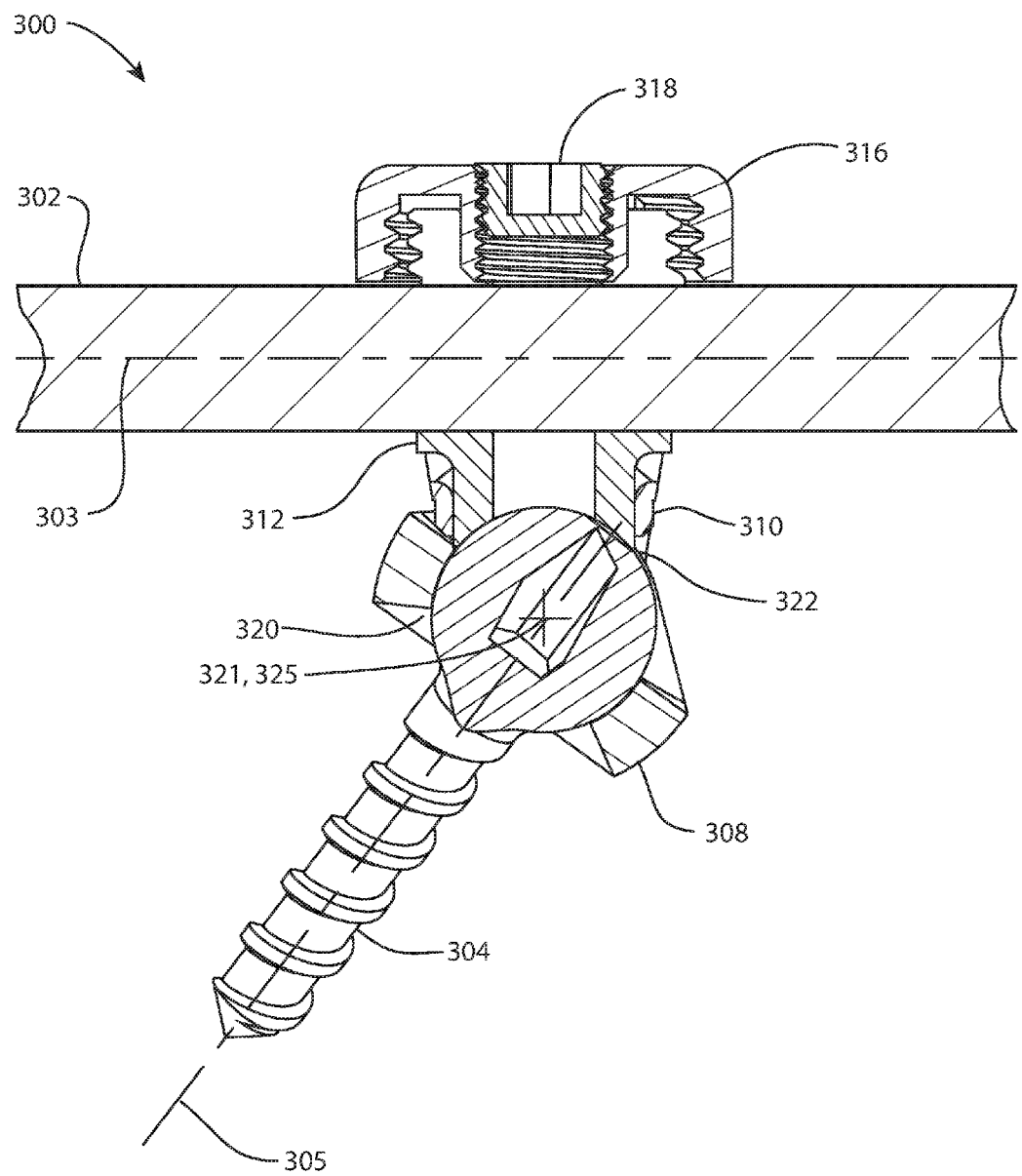
FIG. 4 is a cross section view of the screw and rod system of FIG. 1 taken along section line 4-4 of FIG. 2.
Figure 5:
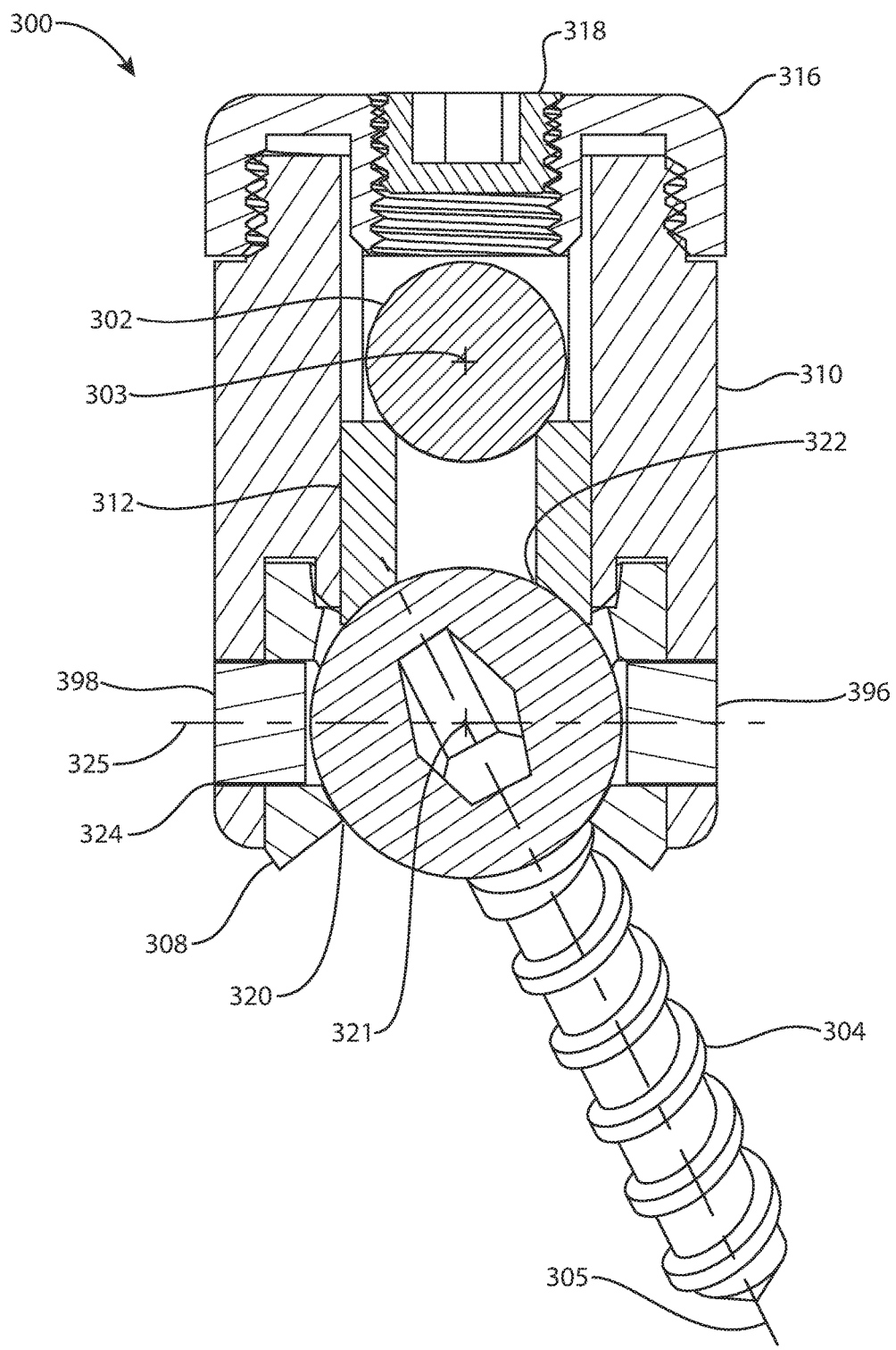
FIG. 5 is a cross section view of the screw and rod system of FIG. 1 taken along section line 5-5 of FIG. 3.
Figure 6:
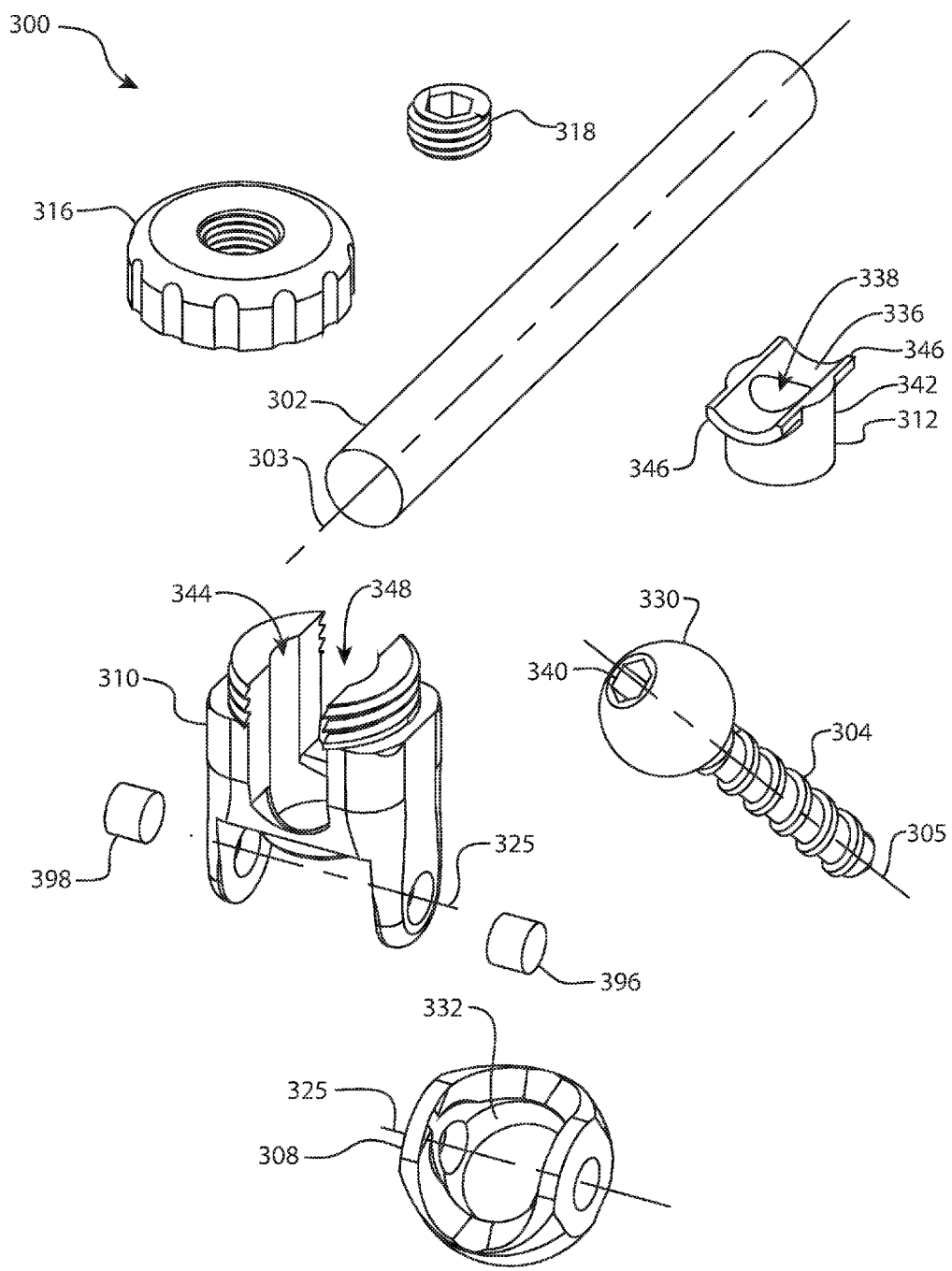
FIG. 6 is an exploded view of the screw and rod system of FIG. 1.
Figure 7:
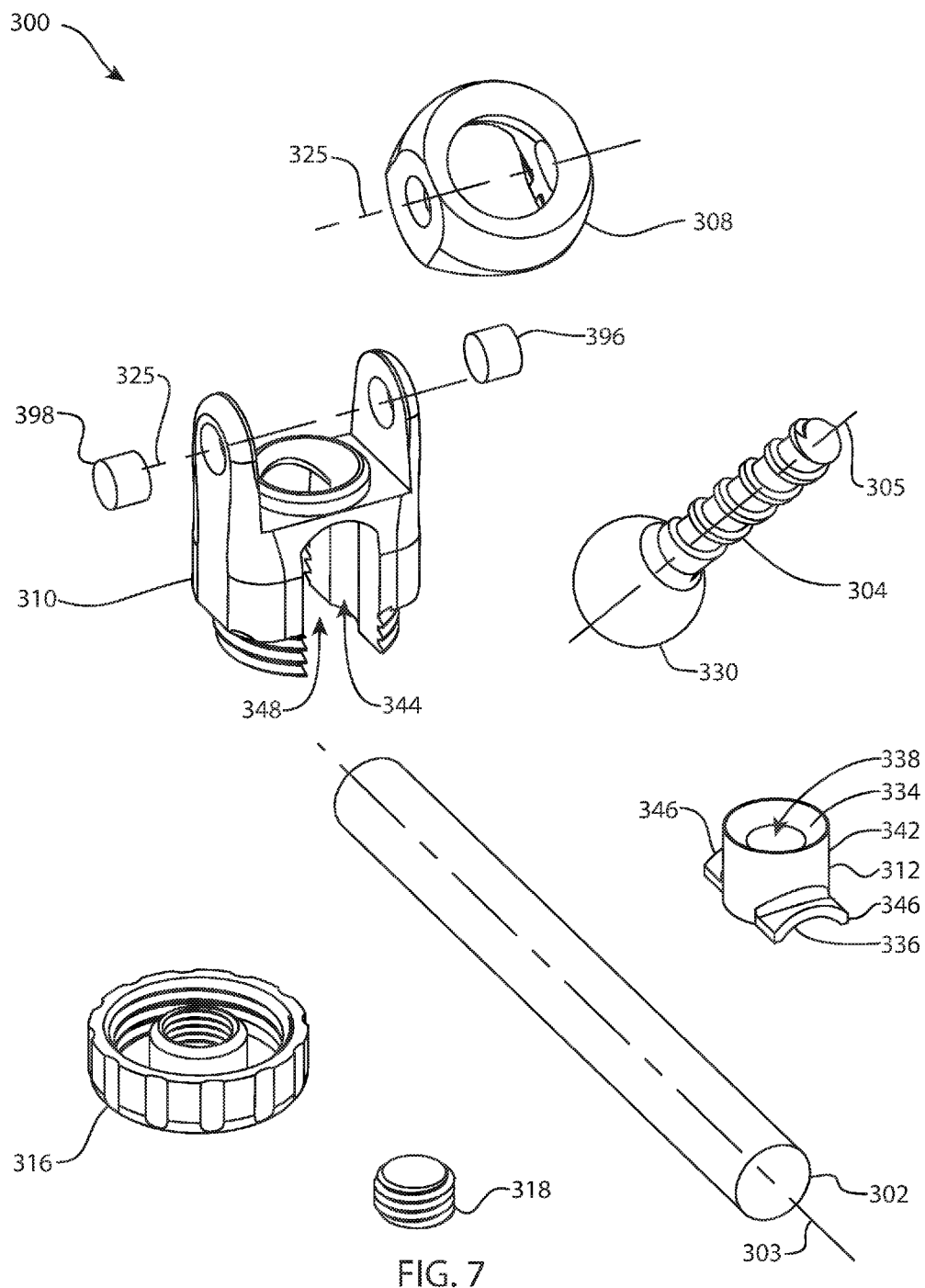
FIG. 7 is another exploded view of the screw and rod system of FIG. 1 from another viewpoint.

Referring to FIGS. 1-7, a screw and rod system 300 includes a rod 302, a screw 304, a carrier 308, a body 310, a lower saddle 312, a cap 316, and a locking element 318. The rod 302 has a central longitudinal axis 303. The screw 304 has a central longitudinal axis 305.

The screw 304 and the carrier 308 form a first joint 320. The first joint 320 may be a ball and socket joint, or a modification thereof, which permits multidirectional or polyaxial rotation of the screw 304 relative to the carrier 308 about a pivot point 321, seen best in FIG. 4. The range of motion of the screw axis 305 relative to the carrier 308 is a cone having its apex coincident with the point 321. The cone may have an included angle of at least 55 degrees, at least 57 degrees, at least 59 degrees, at least 60 degrees, at least 61 degrees, at least 63 degrees, or at least 65 degrees. The first joint 320 may alternately be a hinge joint or another type of joint. The first joint 320 may be formed between a head 330 of the screw 304 and a socket 332 of the carrier 308. The head 330 of the screw 304 and the socket 332 of the carrier 308 may include complementary convex and concave spherical portions which form the first joint 320, as seen best in FIGS. 4-6. The concave spherical portion may instead be a conical socket. The point 321 may be centered in the convex spherical head 330 of the screw 304.

The lower saddle 312 and the head 330 of the screw 304 may form a joint 322. The joint 322 may be a ball and socket joint, or a modification thereof, which permits multidirectional or polyaxial rotation about a point, as illustrated. In this example, the joint 322 permits rotation about the same point 321 as the first joint 320. The joint 322 may be concentric with the first joint 320. The joint 322 may alternately be a hinge joint or another type of joint. The joint 322 may be formed between the head 330 of the screw 304 and a socket 334 of the lower saddle 312. The head 330 of the screw 304 and the socket 334 of the lower saddle 312 may include complementary convex and concave spherical portions which form the joint 322. The concave spherical portion may instead be a conical socket.

The rod 302 rests in a groove 336 of the lower saddle 312. The rod 302 and the lower saddle 312 may have complementary convex and concave cylindrical portions where they make contact. The concave cylindrical portion may instead be a V-groove.

Referring to FIGS. 4-7, the lower saddle 312 is pierced by an opening or hole 338. When the screw 304 and the lower saddle 312 are aligned, the opening 338 provides access for a driver to be inserted into a drive feature 340 of the head 330 of the screw 304 to drive the screw 304 into bone before the rod 302 is installed. The lower saddle 312 includes a cylindrical portion 342 which fits into a cylindrical socket 344 in the body 310 so that the lower saddle 312 is free to translate along the cylindrical socket 344. The lower saddle 312 includes bilateral projections 346 that rest in a slot 348 of the body 310 so that the lower saddle 312 is prevented from rotating relative to the body 310. The slot 348 of the body also receives the rod 302.

The carrier 308 and the body 310 form a second joint 324; one or more pins 396, 398 may also be included in the second joint. The second joint 324 may be a hinge joint, or a modification thereof, which permits rotation about an axis 325. Axis 325 is seen end-on in FIG. 3, and is therefore represented as a point. The second joint 324 may be located beside the first joint 320 and the joint 322, and the point 321 may lie on the axis 325. The range of motion of the carrier 308 relative to the body 310 may have an included angle of at least 35 degrees, at least 37 degrees, at least 39 degrees, at least 40 degrees, at least 41 degrees, at least 43 degrees, or at least 45 degrees. The combination of the first joint 320 and the second joint 324 provides greater angular range of motion between the axis 305 of the screw 304 and the axis 303 of the rod 302, along the axis of the rod, than does a design with only one joint. For example, a first joint 320 having a range of motion with an included angle of 60 degrees and a second joint 324 having a range of motion with an included angle of 40 degrees results in an effective angular range of motion between the screw axis 305 and the rod axis 303 having an included angle of 100 degrees, along the rod axis 303 (i.e., in a plane that includes the rod axis 303 and the pivot point 321 and is perpendicular to the axis 325). For at least this reason, the range of motion of the first joint 320 and the range of motion of the second joint 324 may be called additive because they add together along the rod. The range of motion of the first joint 320 and the range of motion of the second joint 324 may also be called independent, since motion can occur at the first joint 320 without any motion at the second joint 324, and vice versa.

The locking element 318 may be a threaded fastener, or it may include a quarter turn locking mechanism, bayonet connection, or other locking mechanism. The locking element 318 engages the cap 316, which engages the body 310, to provide a compressive force against the rod 302, the lower saddle 312, and the screw 304 within the carrier 308.

The sub-assembly of the carrier 308 and the body 310 may be referred to as a tulip sub-assembly. The tulip sub-assembly may also include the cap 316, the locking element 318, the lower saddle 312, the screw 304, the pin 396, and/or the pin 398.

A method of using the screw and rod system 300 may include the following steps: inserting the screw 304 into the carrier 308 to form the first joint 320; hinging the carrier 308 to the body 310; inserting the lower saddle 312 into the body 310 to form the joint 322, the lower saddle 312 resting on the head 330 of the screw 304; inserting a driver through the opening 338 piercing the lower saddle 312 and into engagement with the drive feature 340 of the head 330 of the screw 304; inserting the screw 304 into bone, the screw 304 carrying the carrier 308, the body 310, and the lower saddle 312; removing the driver; rotating the carrier 308 and/or the body 310 to align the slot 348 of the body 310 with the axis 303 of the rod 302 and to orient the axis 325 transverse to the rod 302; inserting the rod 302 into the slot 348 of the body 310 to rest on the lower saddle 312; engaging the cap 316 with the body 310; inserting the locking element 318 into the cap 316 to rest on the rod 302; partially tightening the locking element 318 to produce a first resistance in the system 300; repositioning the rod 302 relative to the screw 304 by polyaxial rotation of the first joint 320 and/or the joint 322 about the point 321, and/or by rotation of the second joint 324 about the axis 325; and fully tightening the locking element 318 to produce a second resistance in the system 300, wherein the second resistance is greater than the first resistance, wherein the second resistance locks the rod 302, the screw 304, the carrier 308, the body 310, the lower saddle 312, the cap 316, and the locking element 318 together.

Figure 8:
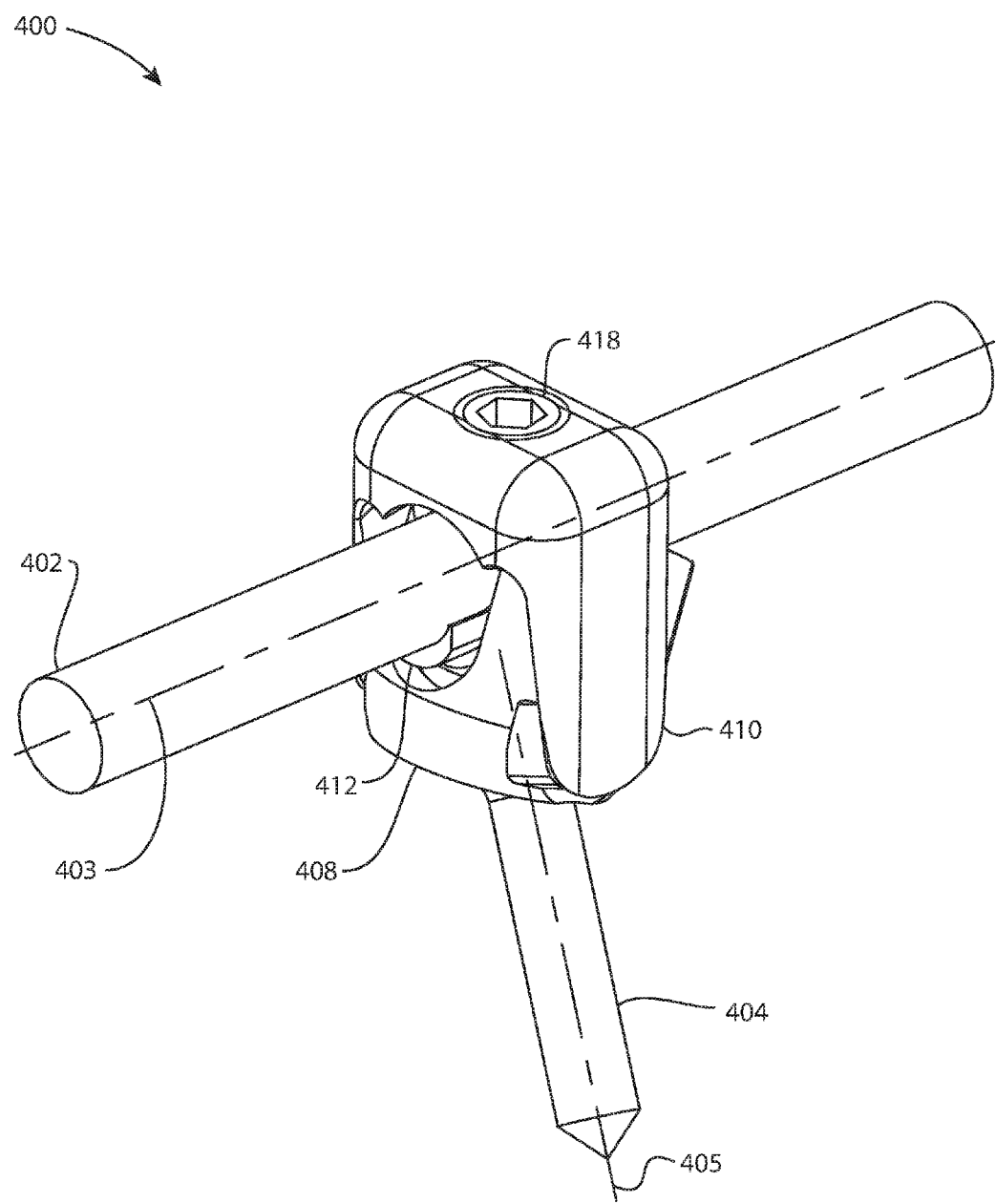
FIG. 8 is an oblique view of a screw and rod system.
Figure 9:
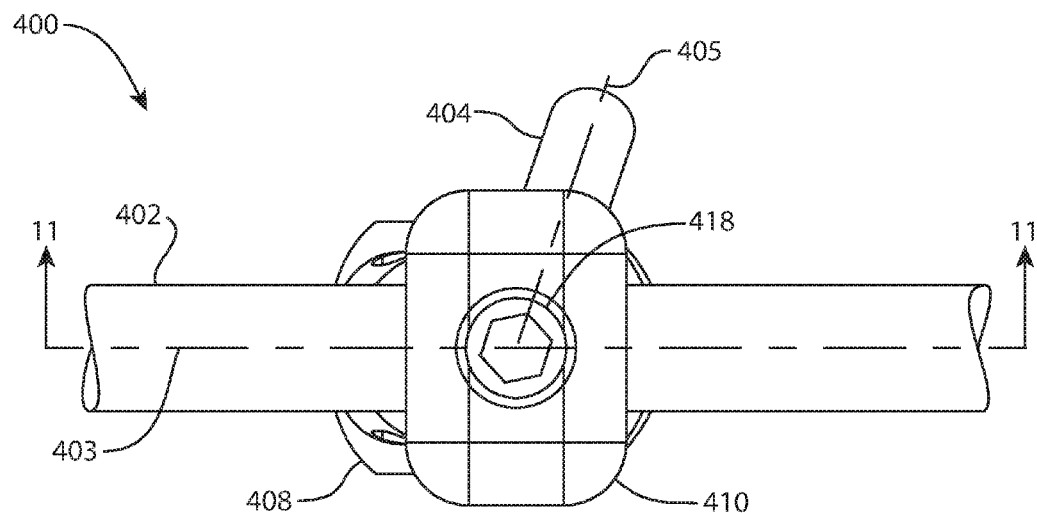
FIG. 9 is a top view of the screw and rod system of FIG. 8.
Figure 10:
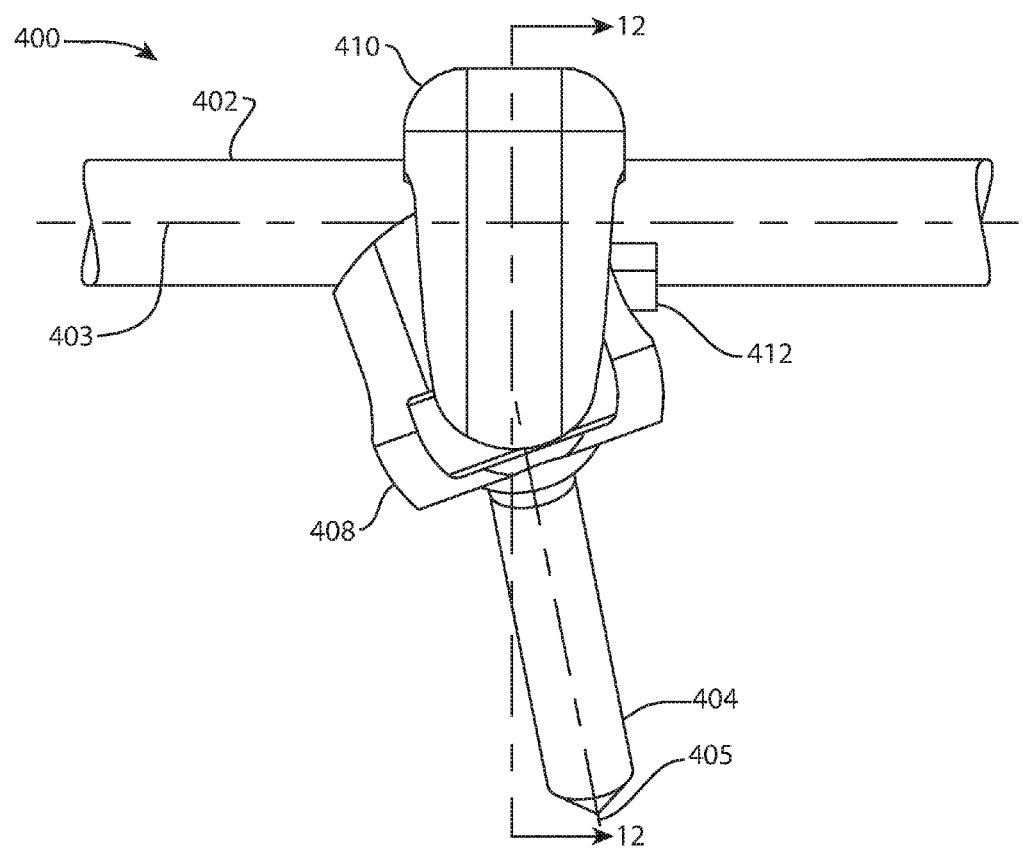
FIG. 10 is a front view of the screw and rod system of FIG. 8.
Figure 11:
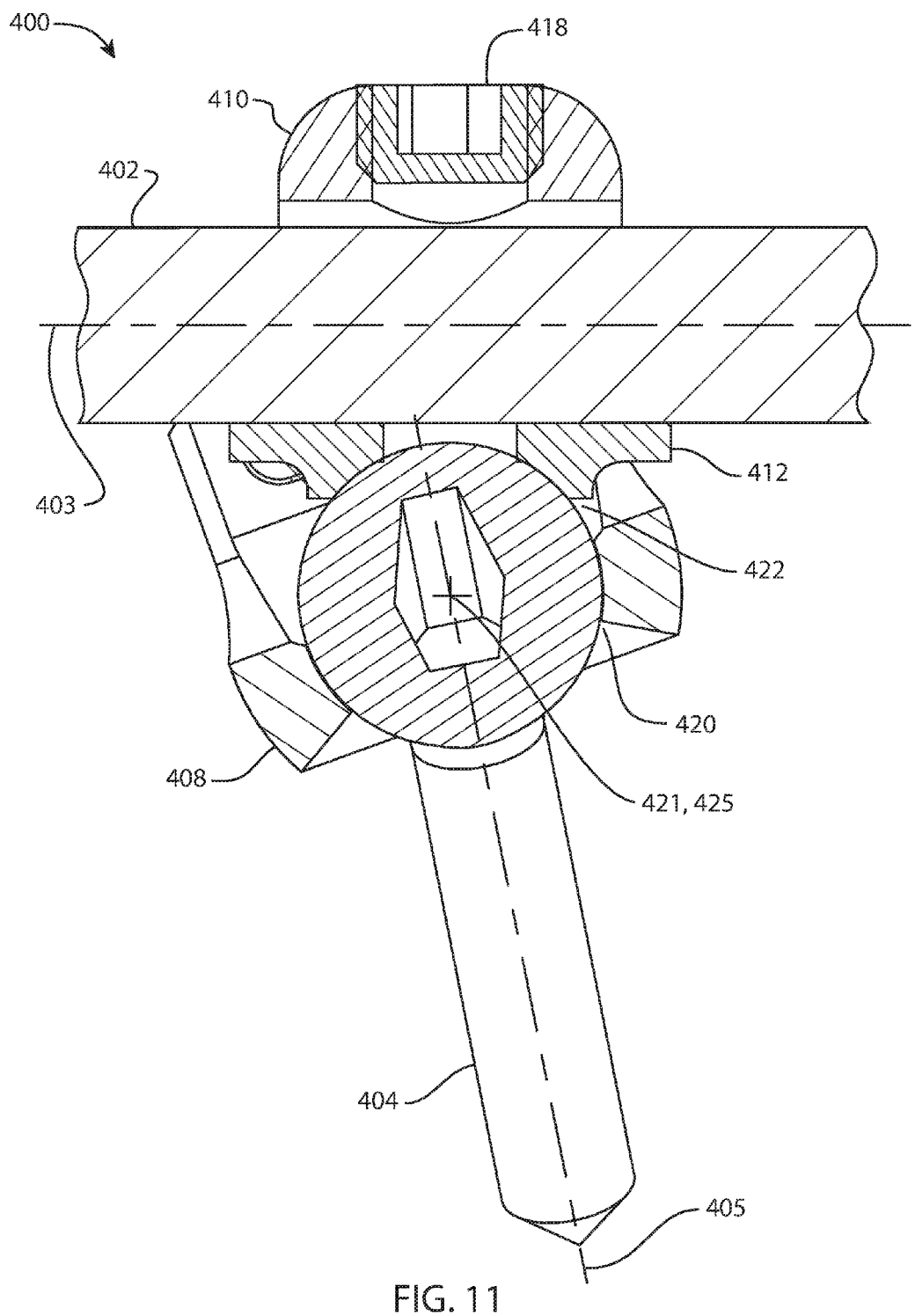
FIG. 11 is a cross section view of the screw and rod system of FIG. 8 taken along section line 4-4 of FIG. 9.
Figure 12:
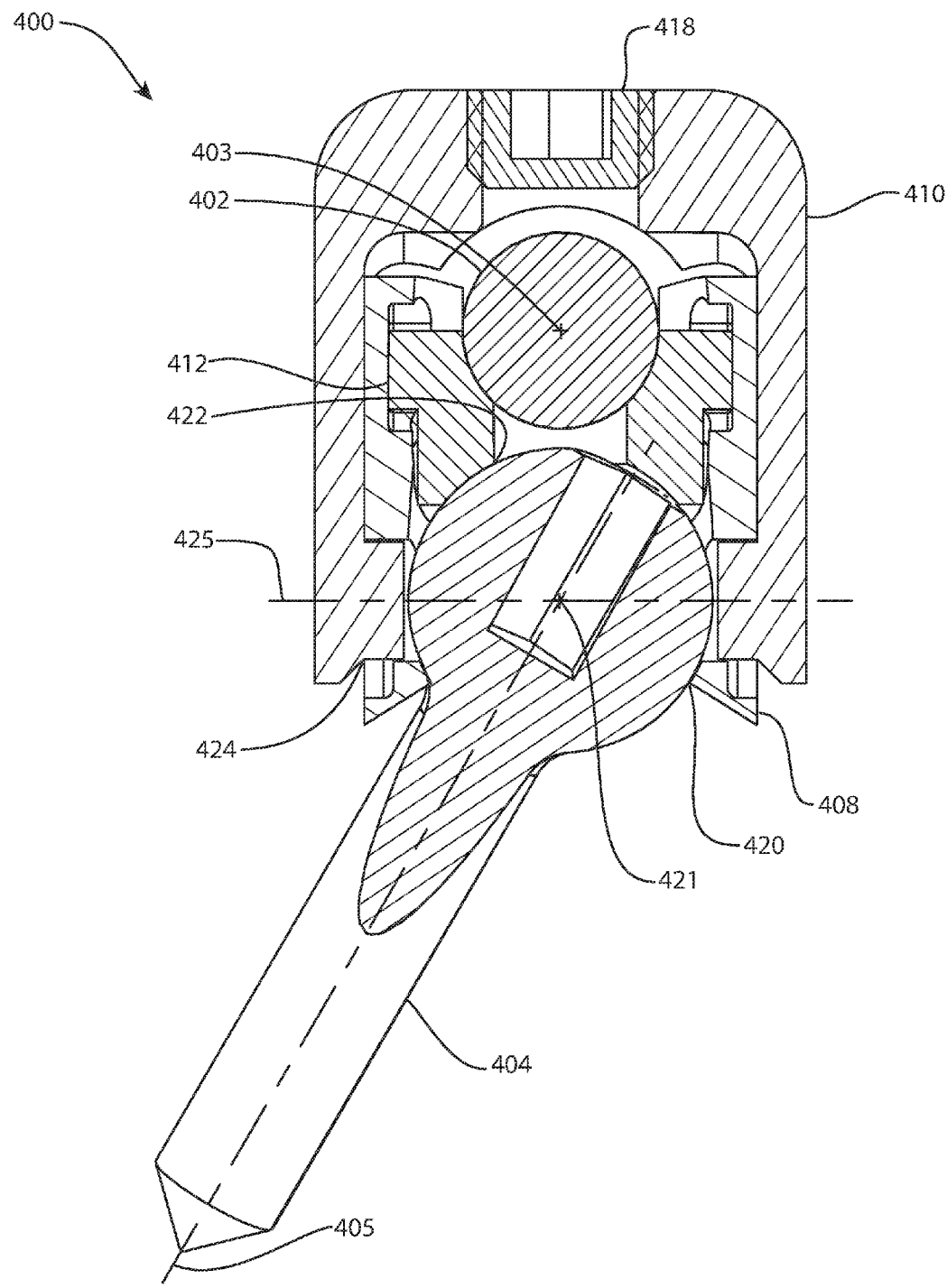
FIG. 12 is a cross section view of the screw and rod system of FIG. 8 taken along section line 5-5 of FIG. 10.
Figure 13:
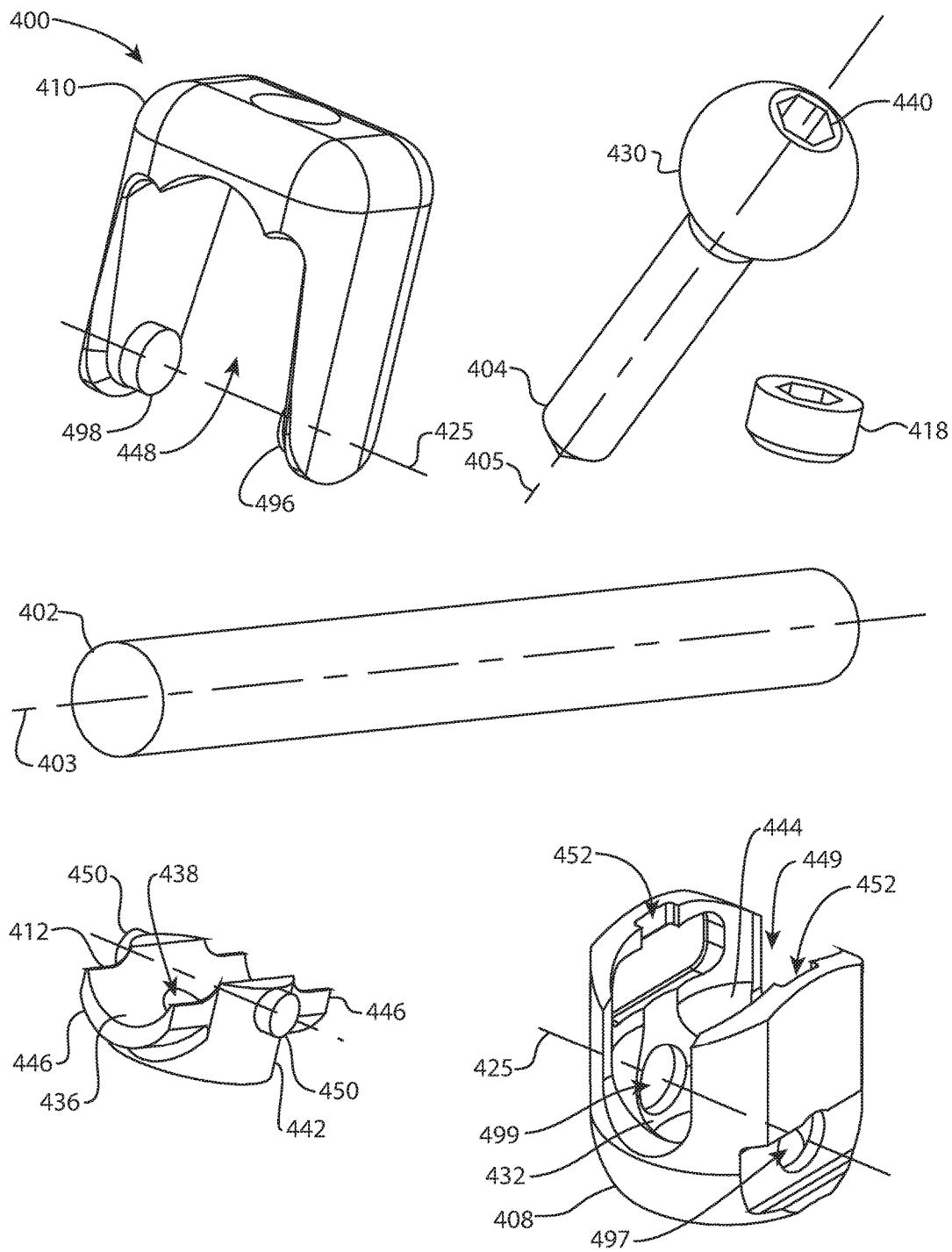
FIG. 13 is an exploded view of the screw and rod system of FIG. 8.
Figure 14:
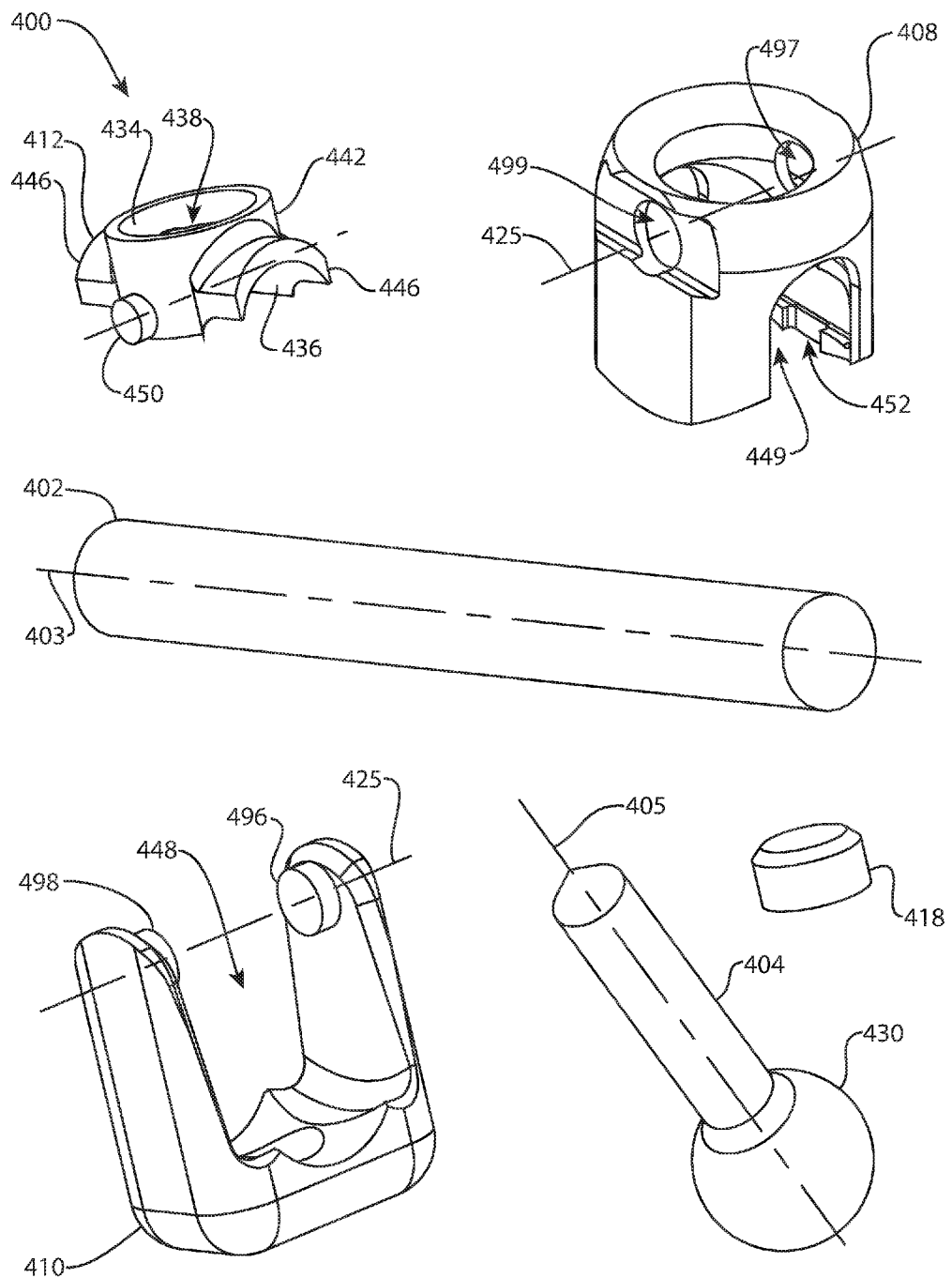
FIG. 14 is another exploded view of the screw and rod system of FIG. 8 from another viewpoint.

Referring to FIGS. 8-14, another screw and rod system 400 includes a rod 402, a screw 404, a carrier 408, a body 410, a lower saddle 412, and a locking element 418. The rod 402 has a central longitudinal axis 403. The screw 404 has a central longitudinal axis 405.

The screw 404 and the carrier 408 form a first joint 420. The first joint 420 may be a ball and socket joint, or a modification thereof, which permits multidirectional or polyaxial rotation of the screw 404 relative to the carrier 408 about a pivot point 421, seen best in FIG. 11. The range of motion of the screw axis 405 relative to the carrier 408 is a cone having its apex coincident with the point 321. The cone may have an included angle of at least 55 degrees, at least 57 degrees, at least 59 degrees, at least 60 degrees, at least 61 degrees, at least 63 degrees, or at least 65 degrees. The first joint 420 may alternately be a hinge joint or another type of joint. The first joint 420 may be formed between a head 430 of the screw 404 and a socket 432 of the carrier 408. The head 430 of the screw 404 and the socket 432 of the carrier 408 may include complementary convex and concave spherical portions which form the first joint 420, as seen best in FIGS. 11-13. The concave spherical portion may instead be a conical socket. The point 421 may be centered in the convex spherical head 430 of the screw 404.

The lower saddle 412 and the head 430 of the screw 404 may form a joint 422. The joint 422 may be a ball and socket joint, or a modification thereof, which permits multidirectional or polyaxial rotation about a point, as illustrated. In this example, the joint 422 permits rotation about the same point 421 as the first joint 420. The joint 422 may be concentric with the first joint 420. The joint 422 may alternately be a hinge joint or another type of joint. The joint 422 may be formed between the head 430 of the screw 404 and a socket 434 of the lower saddle 412. The head 430 of the screw 404 and the socket 434 of the lower saddle 412 may include complementary convex spherical portions which form the joint 422. The concave spherical portion may instead be a conical socket.

The rod 402 rests in a groove 436 of the lower saddle 412. The rod 402 and the lower saddle 412 may have complementary convex and concave cylindrical portions where they make contact. The concave cylindrical portion may instead be a V-groove.

Referring to FIGS. 11-14, the lower saddle 412 is pierced by an opening or hole 438. When the screw 404 and the lower saddle 412 are aligned, the opening 438 provides access for a driver to be inserted into a drive feature 440 of the head 430 of the screw 404 to drive the screw 404 into bone before the rod 402 is installed. The lower saddle 412 includes a cylindrical portion 442 which fits into a cylindrical socket 444 in the carrier 408 so that the lower saddle 412 is free to translate along the cylindrical socket 444. The lower saddle 412 includes bilateral projections 446 that rest in a slot 449 of the carrier 408 so that the lower saddle 412 is prevented from rotating relative to the carrier 408. The slot 449 of the carrier 408 also receives the rod 302. The lower saddle 412 includes bilateral pins 450 that slide in bilateral grooves 452 of the carrier 408. The body 410 includes a slot 448 that receives the rod 402.

The carrier 408 and the body 410 form a second joint 424; one or more pins may also be included in the second joint, and the pins may be separate parts or integrated with the body and/or the carrier. In this example, the second joint 424 may be formed between inwardly-projecting pins 496, 498 of the body 410 and corresponding holes 497, 499 of the carrier 408, as can be appreciated from FIGS. 13 and 14. The second joint 424 may be a hinge joint, or a modification thereof, which permits rotation about an axis 425. The second joint 424 may be located beside the first joint 420 and the joint 422, and the point 421 may lie on the axis 425. The range of motion of the carrier 408 relative to the body 410 may have an included angle of at least 35 degrees, at least 37 degrees, at least 39 degrees, at least 40 degrees, at least 41 degrees, at least 43 degrees, or at least 45 degrees. The combination of the first joint 420 and the second joint 424 provides greater angular range of motion between the axis 405 of the screw 404 and the axis 403 of the rod 402, along the axis of the rod, than does a design with only one joint. For example, a first joint 420 having a range of motion with an included angle of 60 degrees and second joint 424 having a range of motion with an included angle of 40 degrees results in an effective angular range of motion between the screw axis 405 and the rod axis 403 having an included angle of 100 degrees, along the rod axis 403 (i.e., in a plant that includes the rod axis 403 and the pivot point 421 and is perpendicular to the axis 425). For at least this reason, the range of motion of the first joint 420 and the range of motion of the second joint 424 may be called additive because they add together along the rod. The range of motion of the first joint 420 and the range of motion of the second joint 424 may also be called independent, since motion can occur at the first joint 420 without any motion at the second joint 424, and vice versa.

The locking element 418 may be a threaded fastener, or it may include a quarter turn locking mechanism, bayonet connection, or other locking mechanism. The locking element 418 engages the body 410 to provide a compressive force against the rod 402, the lower saddle 412, and the screw 404 within the carrier 408.

The sub-assembly of the carrier 408 and the body 410 may be referred to as a tulip sub-assembly. The tulip sub-assembly may also include the locking element 418, the lower saddle 412, and/or the screw 404.

A method of using the screw and rod system 400 may include the following steps: inserting the screw 404 into the carrier 408 to form the first joint 420; inserting the lower saddle 412 into the carrier 408 to form the joint 422, the lower saddle 412 resting on the head of the screw 404; inserting a driver through the opening 438 piercing the lower saddle 412 and into engagement with the drive feature 440 of the head 430 of the screw 404; inserting the screw 404 into bone, the screw 404 carrying the carrier 408 and the lower saddle 412; removing the driver; rotating the carrier 408 to align the slot 449 with the axis of the rod 402 and to orient the axis 425 transverse to the rod 402; inserting the rod 402 into the slot 449 of the carrier 408 to rest on the lower saddle 412; hinging the carrier 408 to the body 410; inserting the locking element 418 into the body 410 to rest on the rod 402; partially tightening the locking element 418 to produce a first resistance in the system 400; repositioning the rod 402 relative to the screw 404 by polyaxial rotation of the first joint 420 and/or the joint 422 about the point 421, and/or by rotation of the second joint 424 about the axis 425; and fully tightening the locking element 418 to produce a second resistance in the system 400, wherein the second resistance is greater than the first resistance, wherein the second resistance locks the rod 402, the screw 404, the carrier 408, the body 410, the lower saddle 412, and the locking element 418 together.

Figure 15:
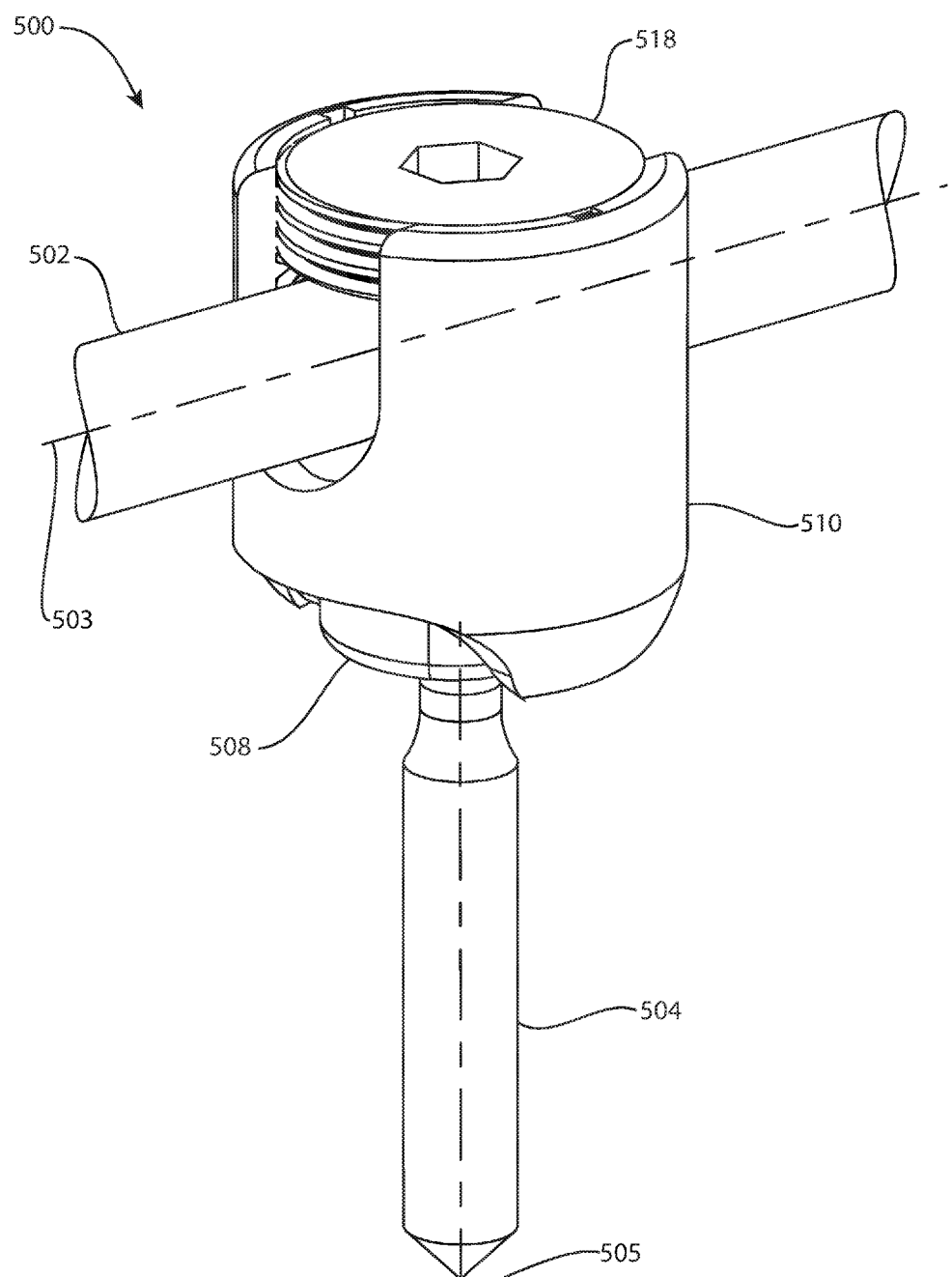
FIG. 15 is an oblique view of a screw and rod system.
Figure 16:
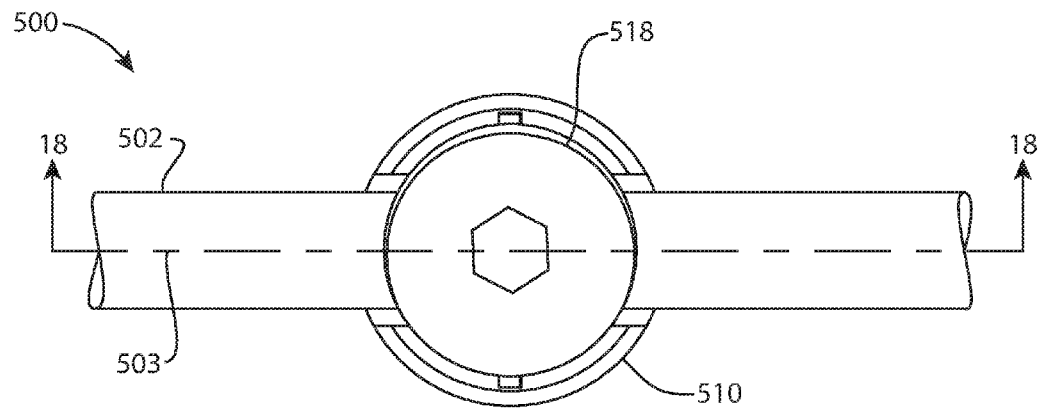
FIG. 16 is a top view of the screw and rod system of FIG. 15.
Figure 17:
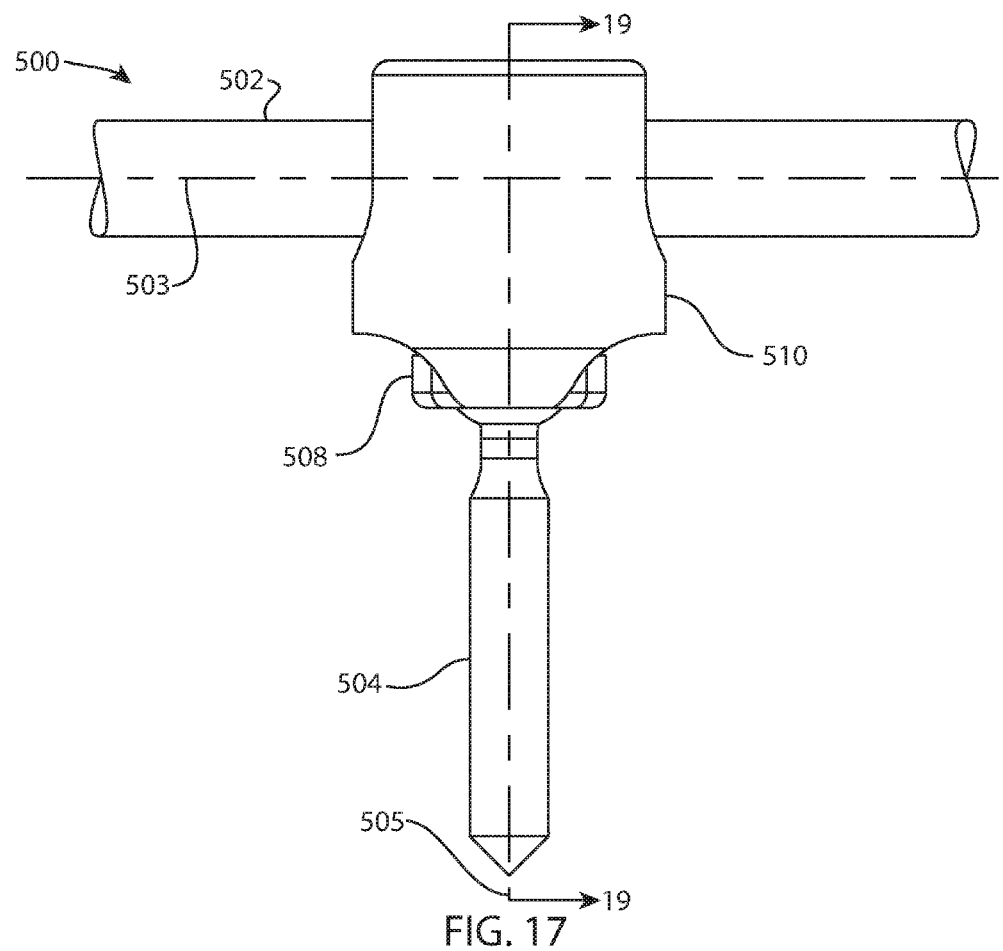
FIG. 17 is a front view of the screw and rod system of FIG. 15.
Figure 18:
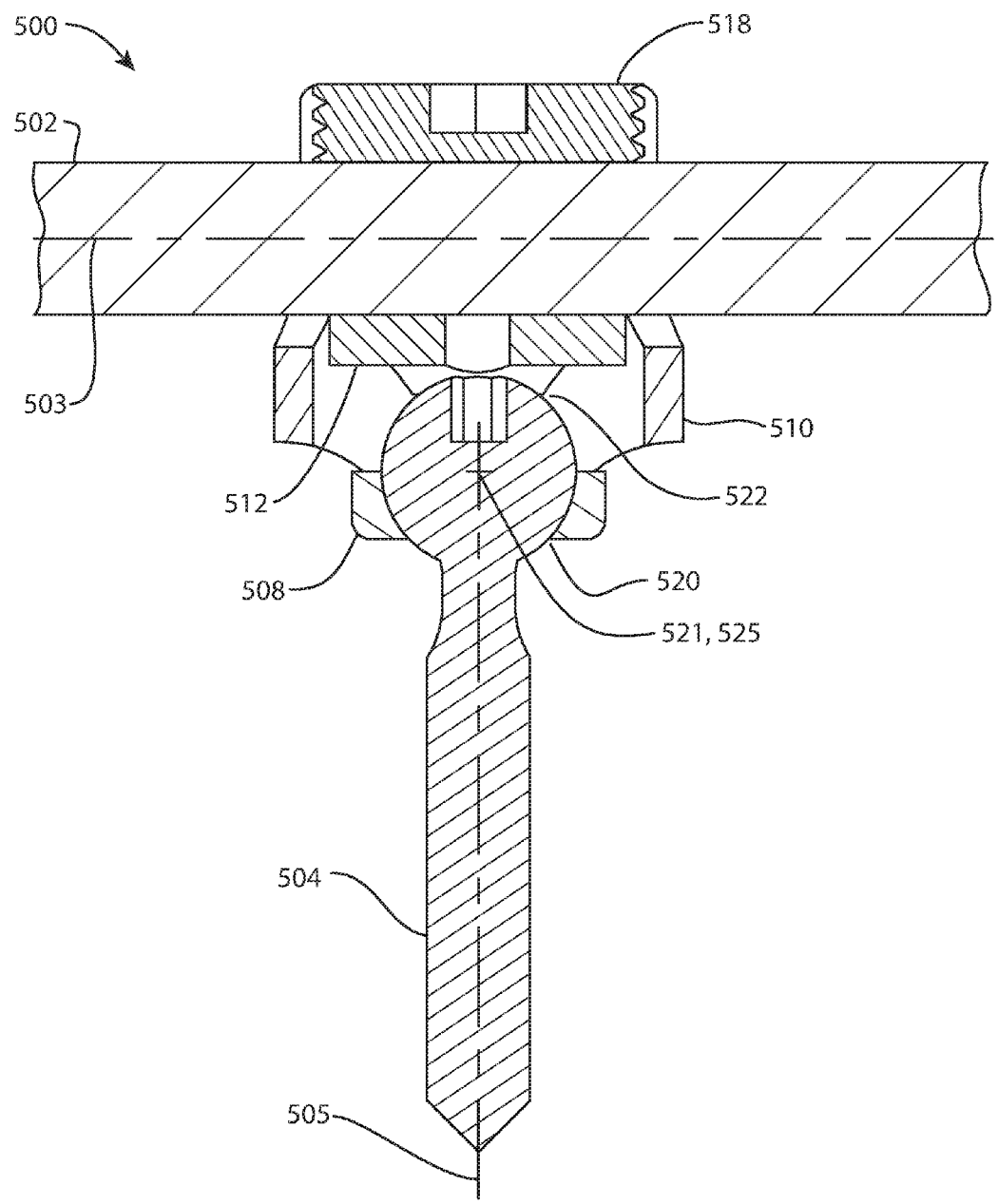
FIG. 18 is a cross section view of the screw and rod system of FIG. 15 taken along section line 4-4 of FIG. 16.
Figure 19:
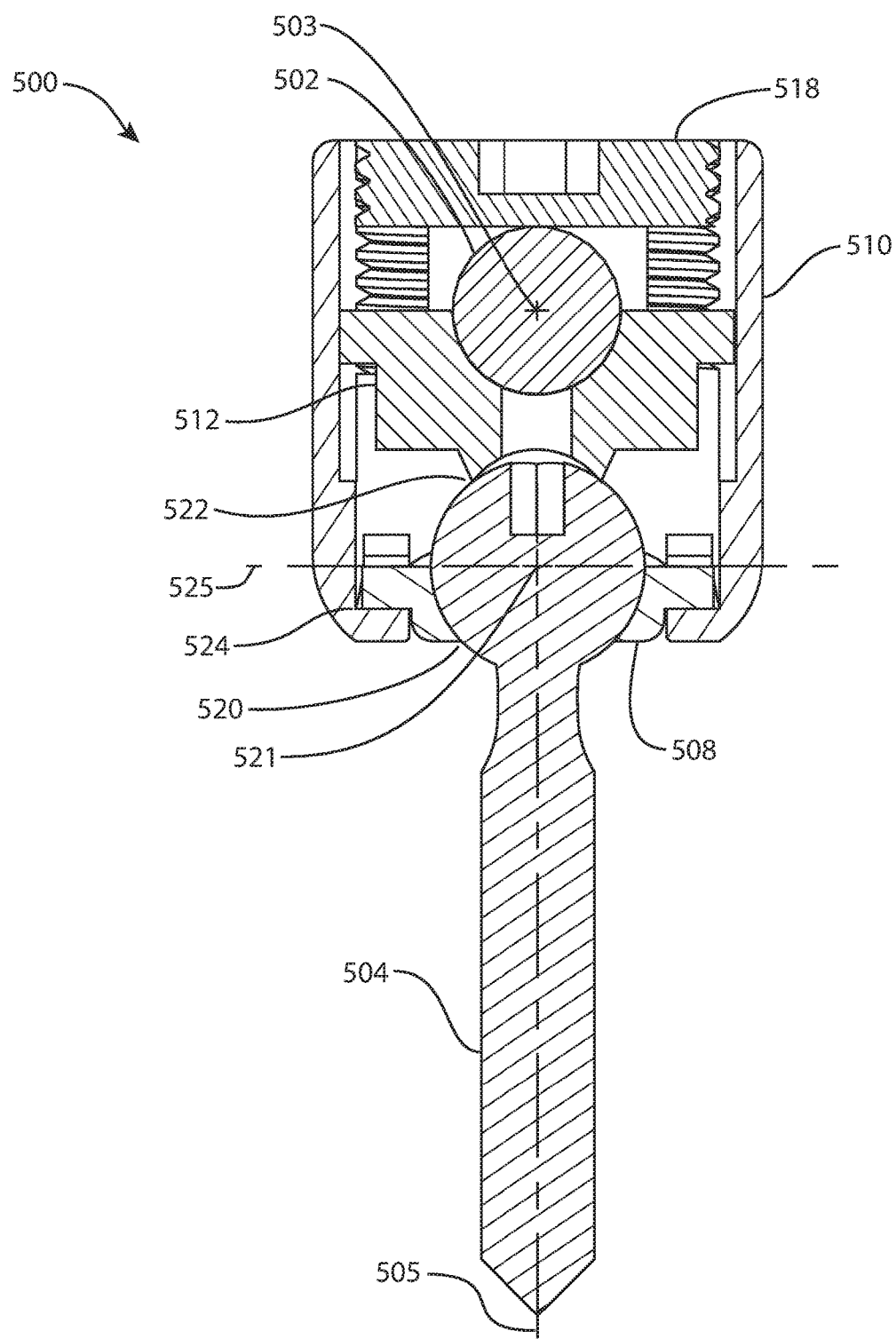
FIG. 19 is a cross section view of the screw and rod system of FIG. 15 taken along section line 5-5 of FIG. 17.
Figure 20:
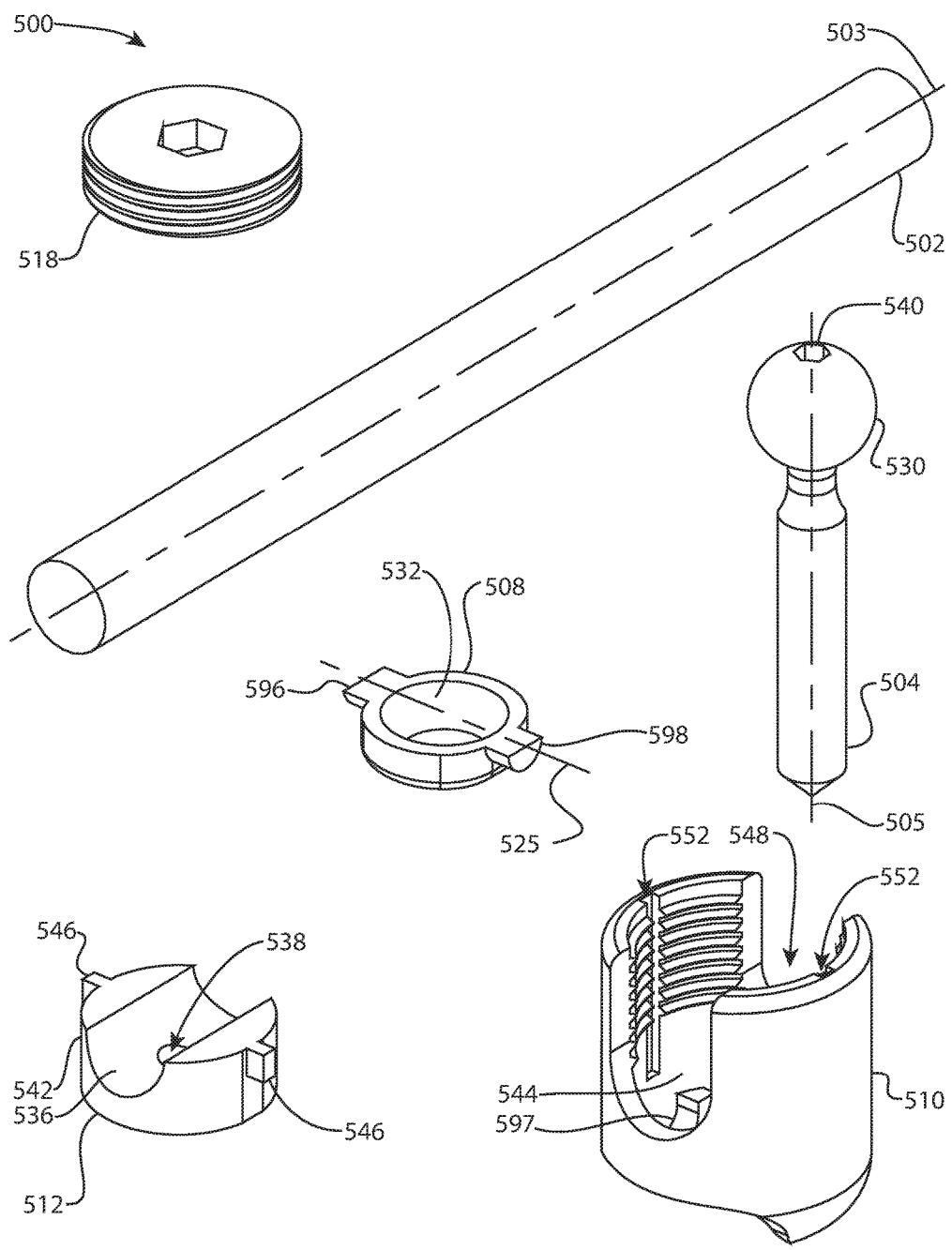
FIG. 20 is an exploded view of the screw and rod system of FIG. 15.
Figure 21:
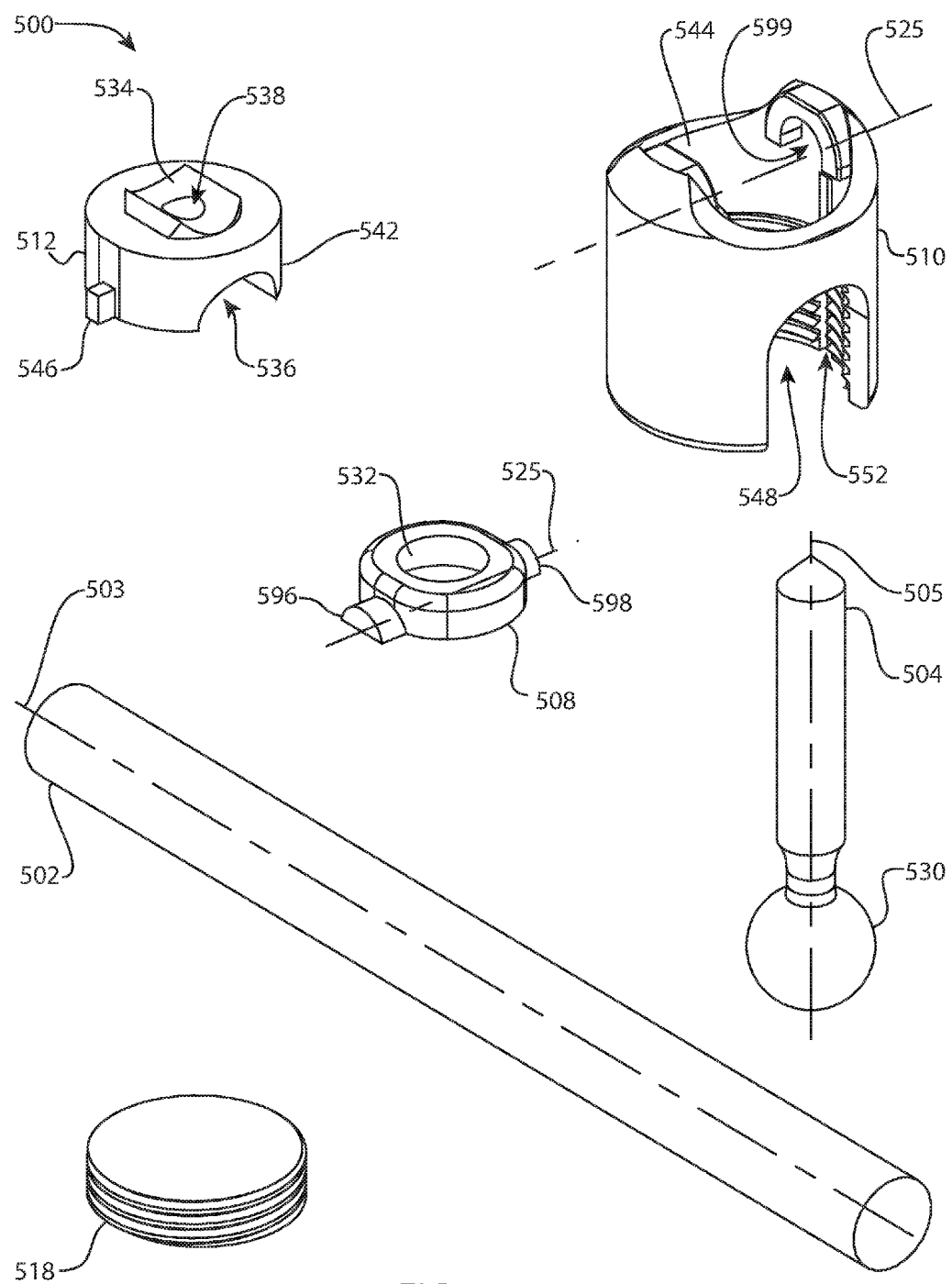
FIG. 21 is another exploded view of the screw and rod system of FIG. 15 from another viewpoint.

Referring to FIGS. 15-21, yet another screw and rod system 500 includes a rod 502, a screw 504, a carrier 508, a body 510, a lower saddle 512, and a locking element 518. The rod 502 has a central longitudinal axis 503. The screw 504 has a central longitudinal axis 505.

The screw 504 and the carrier 508 form a first joint 520. The first joint 520 may be a ball and socket joint, or a modification thereof, which permits multidirectional or polyaxial rotation of the screw 504 relative to the carrier 508 about a pivot point 521, seen best in FIGS. 18 and 19. The range of motion of the screw axis 505 relative to the carrier 508 is a cone having its apex coincident with the point 521. The cone may have an included angle of at least 55 degrees, at least 57 degrees, at least 59 degrees, at least 60 degrees, at least 61 degrees, at least 63 degrees, or at least 65 degrees. The first joint 520 may alternately be a hinge joint or another type of joint. The first joint 520 may be formed between a head 530 of the screw 504 and a socket 532 of the carrier 508. The head 530 of the screw 504 and the socket 532 of the carrier 508 may include complementary convex and concave spherical portions which form the first joint 520, as seen best in FIGS. 18-21. The concave spherical portion may instead be a conical socket. The point 521 may be centered in the convex spherical head 530 of the screw 504.

The lower saddle 512 and the head 530 of the screw 504 may form a joint 522. The joint 522 may be a ball and socket joint, or a modification thereof, which permits multidirectional or polyaxial rotation about a point, as illustrated. In this example, the joint 522 permits rotation about the same point 521 as the first joint 520. The joint 522 may be concentric with the first joint 520. The joint 522 may alternately be a hinge joint or another type of joint. The joint 522 may be formed between the head 530 of the screw 504 and a groove 534 of the lower saddle 512. The groove 534 of the lower saddle 512 may include a concave cylindrical portion for contact with the screw head 530; the screw head 530 and the concave cylindrical portion of the groove 534 form the joint 522. The concave cylindrical portion may instead be a conical socket, a concave spherical portion, a V-groove, or another shape.

The rod 502 rests in a groove 536 of the lower saddle 512. The rod 502 and the lower saddle 512 may have complementary convex and concave cylindrical portions where they make contact. The concave cylindrical portion may instead be a V-groove.

Referring to FIGS. 18-21, the lower saddle 512 is pierced by an opening or hole 538. When the screw 504 and the lower saddle 512 are aligned, the opening 538 provides access for a driver to be inserted into the drive feature 540 of the head 530 of the screw 504 to drive the screw 504 into bone before the rod 502 is installed. The lower saddle 512 includes a cylindrical portion 542 which fits into a cylindrical socket 544 in the body 510 so that the lower saddle 512 is free to translate along the cylindrical socket 544. The lower saddle 512 includes bilateral projections 546 that rest in bilateral grooves 552 of the body 510 so that the lower saddle 512 is prevented from rotating relative to the body 510. The body 510 includes a slot 548 that receives the rod 502.

The carrier 508 and the body 510 form a second joint 524; one or more pins may also be included in the second joint, and the pins may be separate parts or integrated with the body and/or the carrier. In this example, the second joint 524 may be formed between outwardly-projecting pins 496, 498 (half pins are shown) of the carrier 508 and corresponding supports 497, 499 of the body 510, as can be appreciated from FIGS. 20 and 21. The second joint 524 may be a hinge joint, or a modification thereof, which permits rotation about an axis 525. Axis 525 is seen best in FIG. 19. The second joint 524 may be located beside the first joint 520 and the joint 522, and the point 521 may lie on the axis 525. The range of motion of the carrier 508 relative to the body 510 may have an included angle of at least 35 degrees, at least 37 degrees, at least 39 degrees, at least 40 degrees, at least 41 degrees, at least 43 degrees, or at least 45 degrees. The combination of the first joint 520 and the second joint 524 provides greater angular range of motion between the axis 505 of the screw 504 and the axis 503 of the rod 502, along the axis of the rod, than does a design with only one joint. For example, a first joint 520 having a range of motion with an included angle of 60 degrees and a second joint 524 having a range of motion with an included angle of 40 degrees results in an effective angular range of motion between the screw axis 505 and the rod axis 503 having an included angle of 100 degrees, along the rod axis 503 (i.e., in a plane that includes the rod axis 503 and the pivot point 521 and is perpendicular to the axis 525). For at least this reason, the range of motion of the first joint 520 and the range of motion of the second joint 524 may be called additive because they add together along the rod. The range of motion of the first joint 520 and the range of motion of the second joint 524 may also be called independent, since motion can occur at the first joint 520 without any motion at the second joint 524, and vice versa The locking element 518 may be a threaded fastener, or it may include a quarter turn locking mechanism, bayonet connection, or other locking mechanism. The locking element 518 engages the body 510 to provide a compressive force against the rod 502, the lower saddle 512, and the screw 504 within the carrier 508.

The sub-assembly of the carrier 508 and the body 510 may be referred to as a tulip sub-assembly. The tulip sub-assembly may also include the locking element 518, the lower saddle 512, and/or the screw 504.

A method of using the screw and rod system 500 may include the following steps: inserting the screw 504 into the carrier 508 to form the first joint 520; hinging the carrier 508 to the body 510; inserting the lower saddle 512 into the body 510 to form the joint 522, the lower saddle 512 resting on the head of the screw 504; inserting a driver through the opening 538 piercing the lower saddle 512 and into engagement with the drive feature 540 of the head 530 of the screw 504; inserting the screw 504 into bone, the screw 504 carrying the carrier 508, the body 510, and the lower saddle 512; removing the driver; rotating the carrier 508 and/or the body 510 to align the slot 548 of the body 510 with the axis 503 of the rod 502 and to orient the axis 525 transverse to the rod 502; inserting the rod 502 into the slot 548 of the body 510 to rest on the lower saddle 512; inserting the locking element 518 into the body 510 to rest on the rod 502; partially tightening the locking element 518 to produce a first resistance in the system 500; repositioning the rod 502 relative to the screw 504 by polyaxial rotation of the first joint 520 and/or the joint 522 about the point 521, and/or by rotation of the second joint 524 about the axis 525; and fully tightening the locking element 518 to produce a second resistance in the system 500, wherein the second resistance is greater than the first resistance, wherein the second resistance locks the rod 502, the screw 504, the carrier 508, the body 510, the lower saddle 512, and the locking element 518 together.

Figure 22:
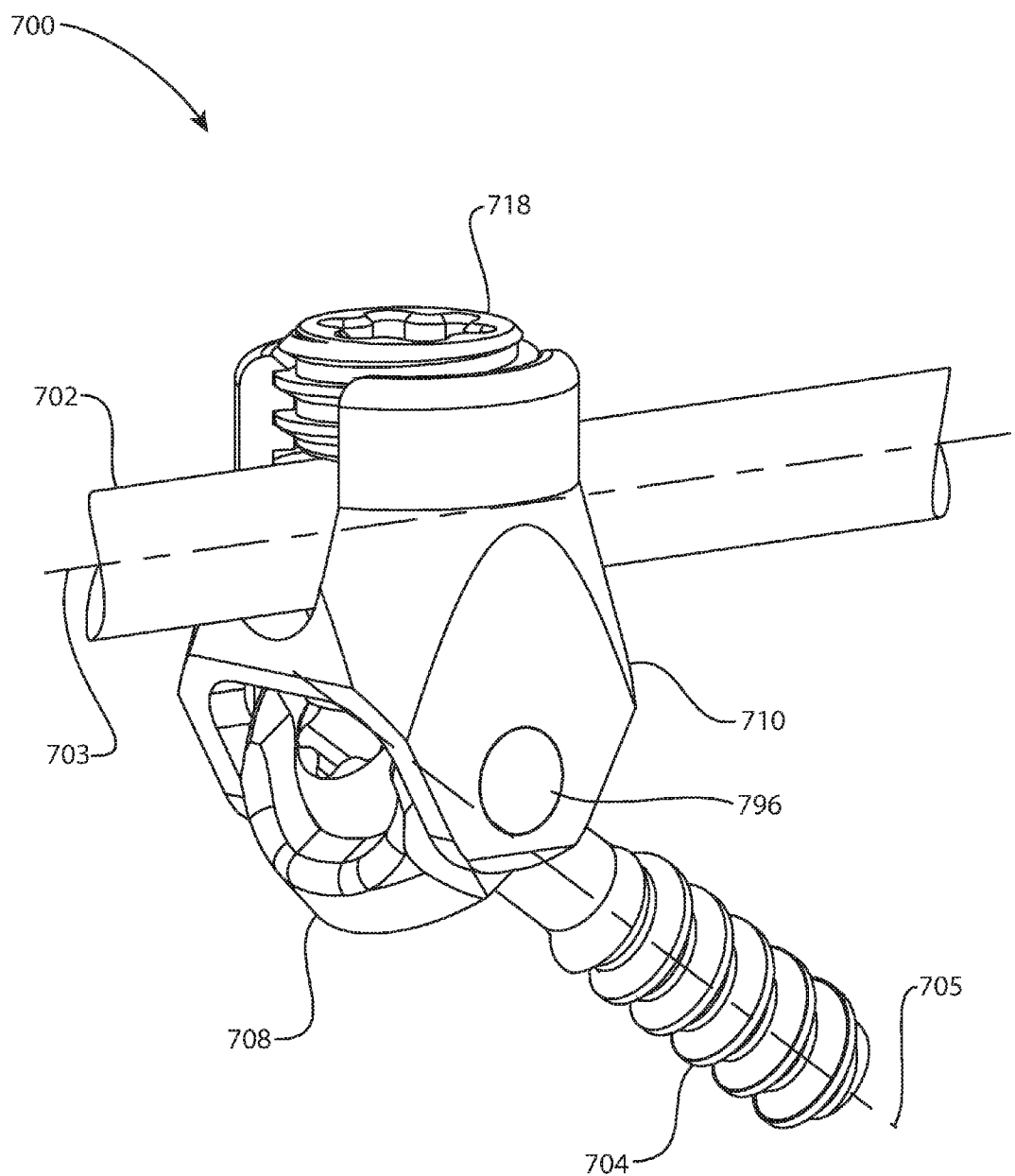
FIG. 22 is an oblique view of a screw and rod system.
Figure 23:
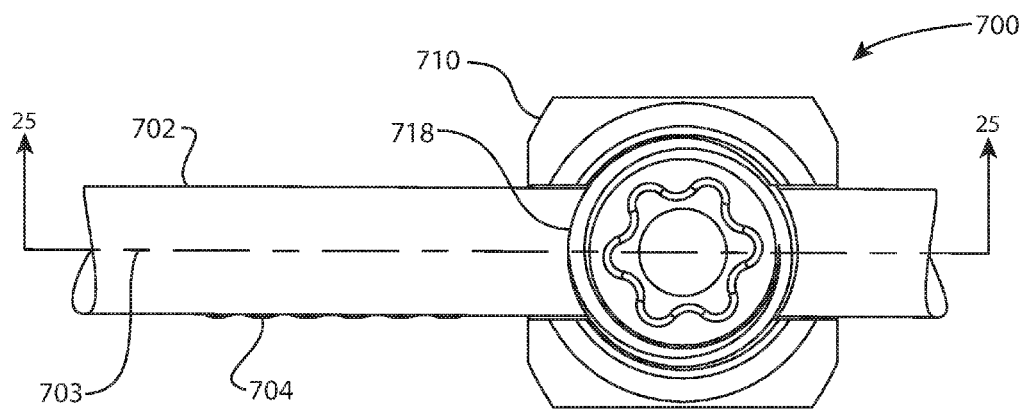
FIG. 23 is a top view of the screw and rod system of FIG. 22.
Figure 24:
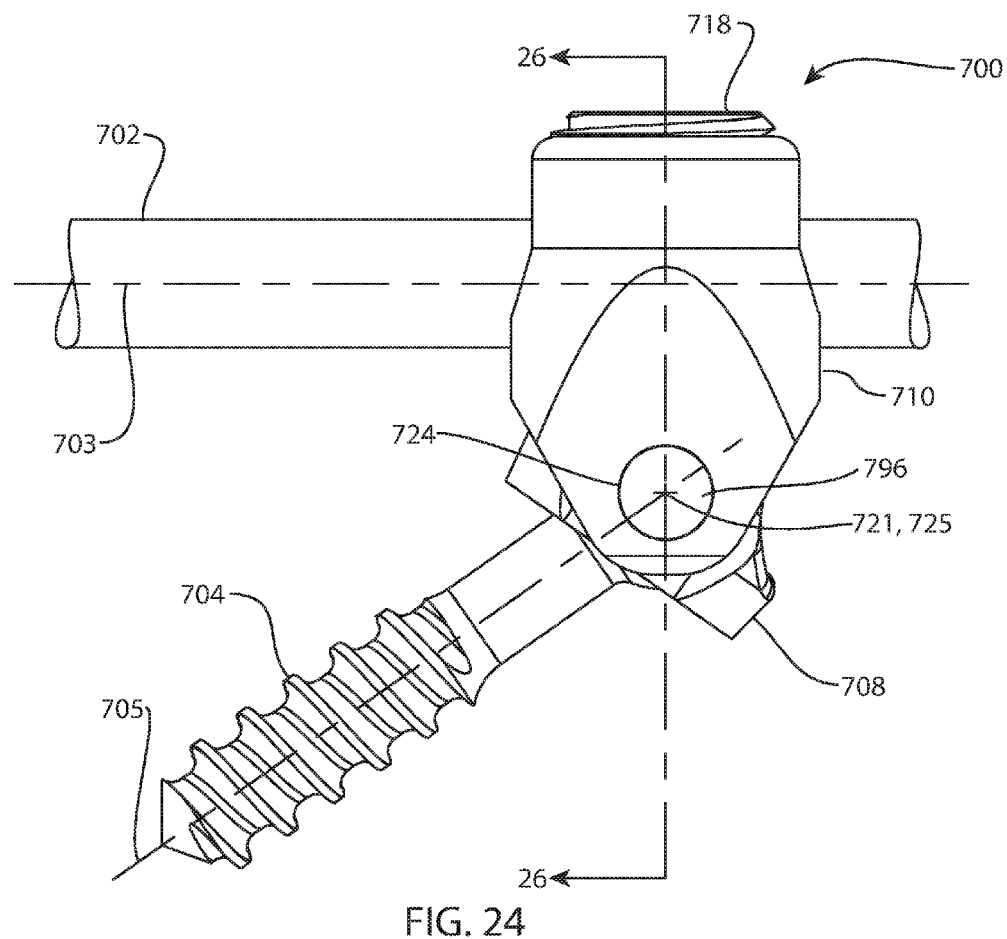
FIG. 24 is a front view of the screw and rod system of FIG. 22.
Figure 25:
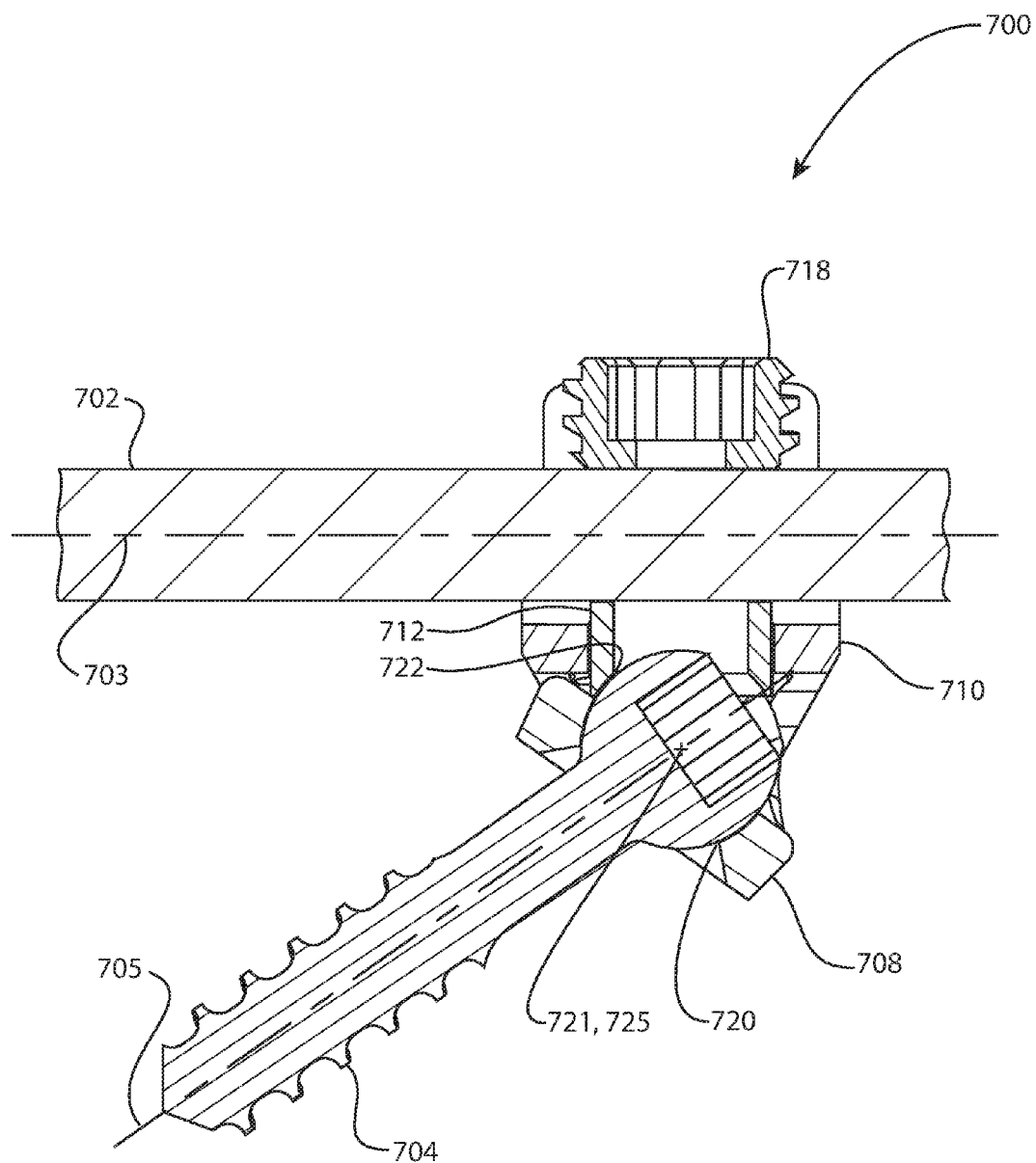
FIG. 25 is a cross section view of the screw and rod system of FIG. 22 taken along section line 4-4 of FIG. 23.
Figure 26:
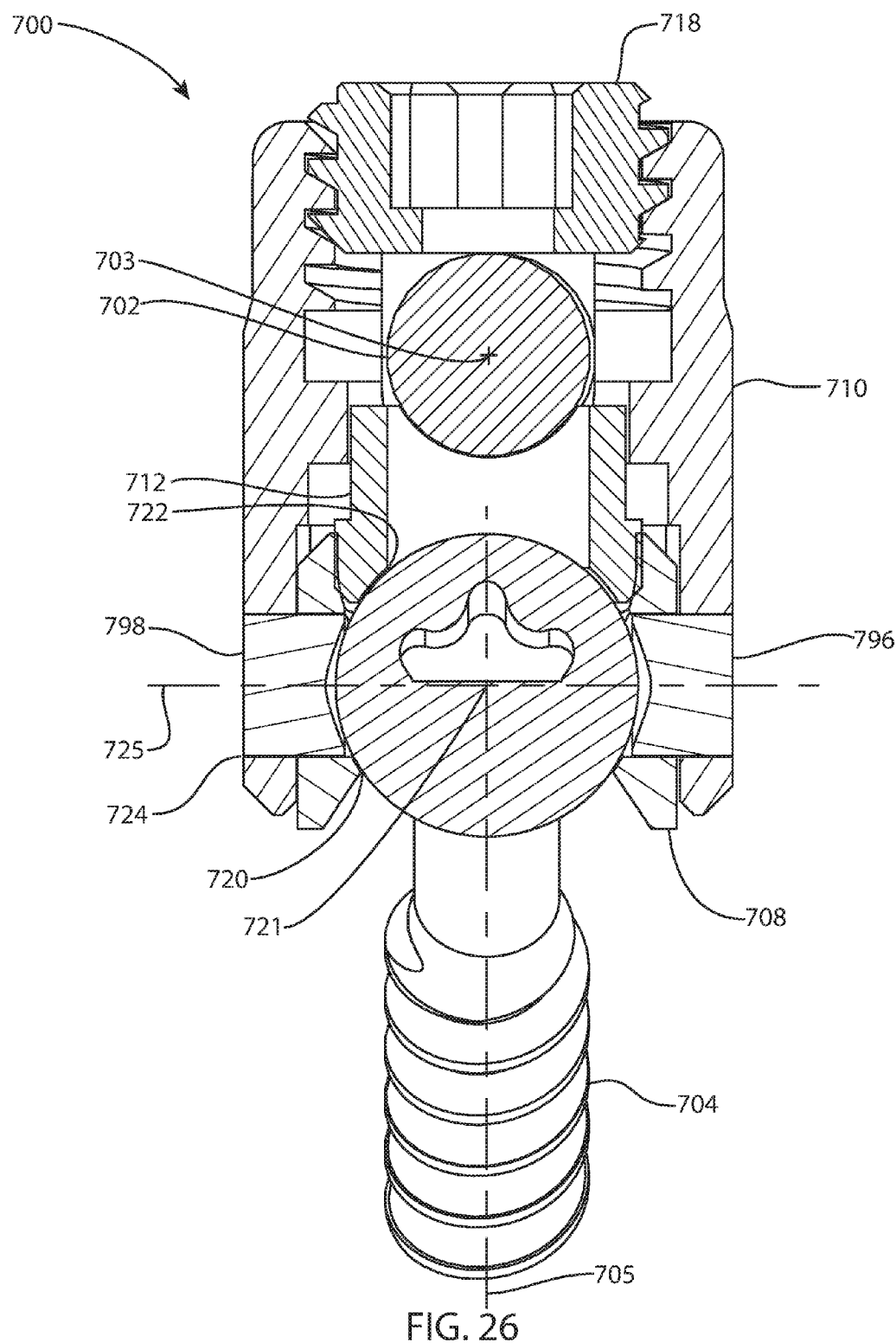
FIG. 26 is a cross section view of the screw and rod system of FIG. 22 taken along section line 5-5 of FIG. 24.
Figure 27:
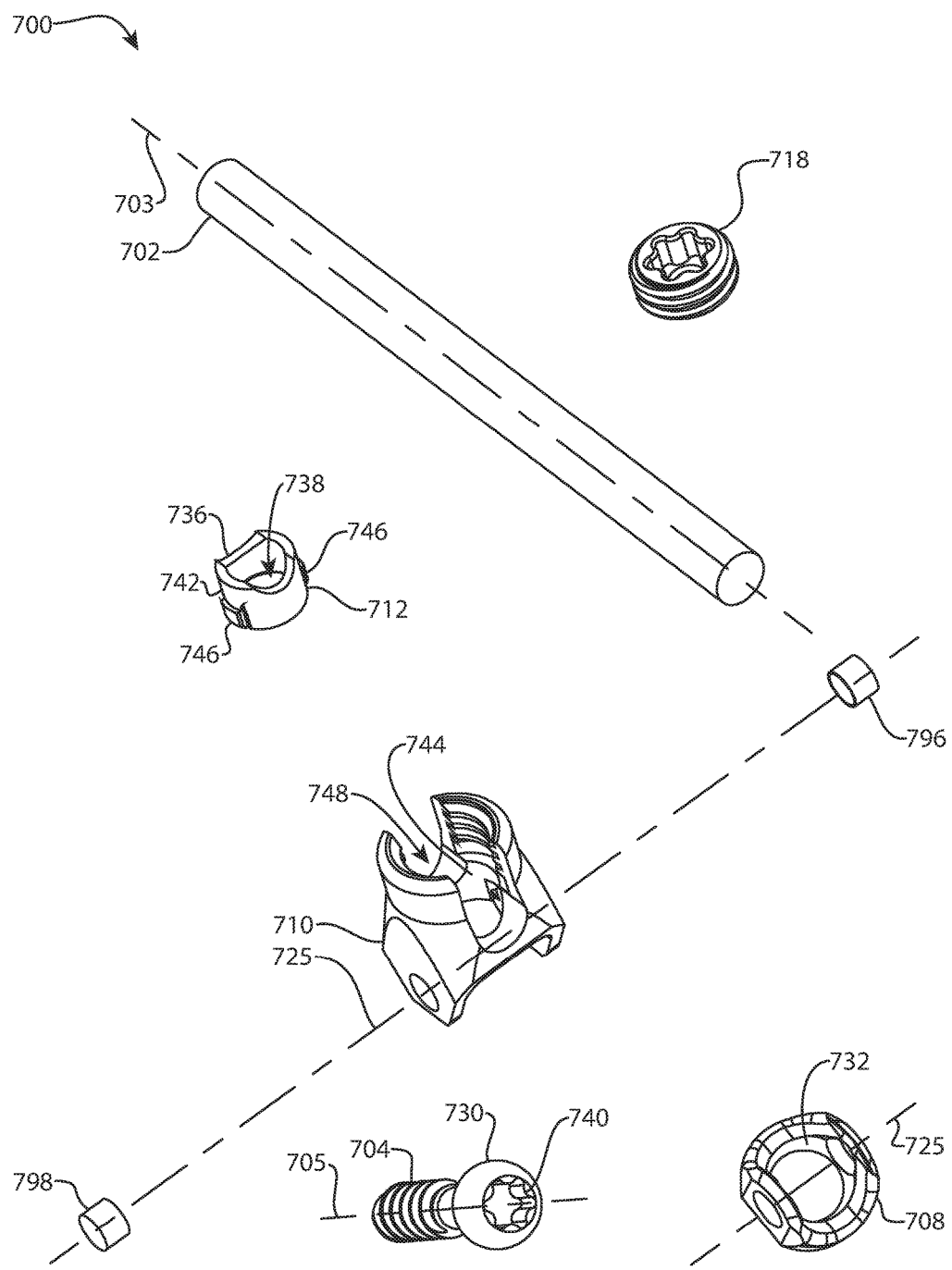
FIG. 27 is an exploded view of the screw and rod system of FIG. 22.
Figure 28:
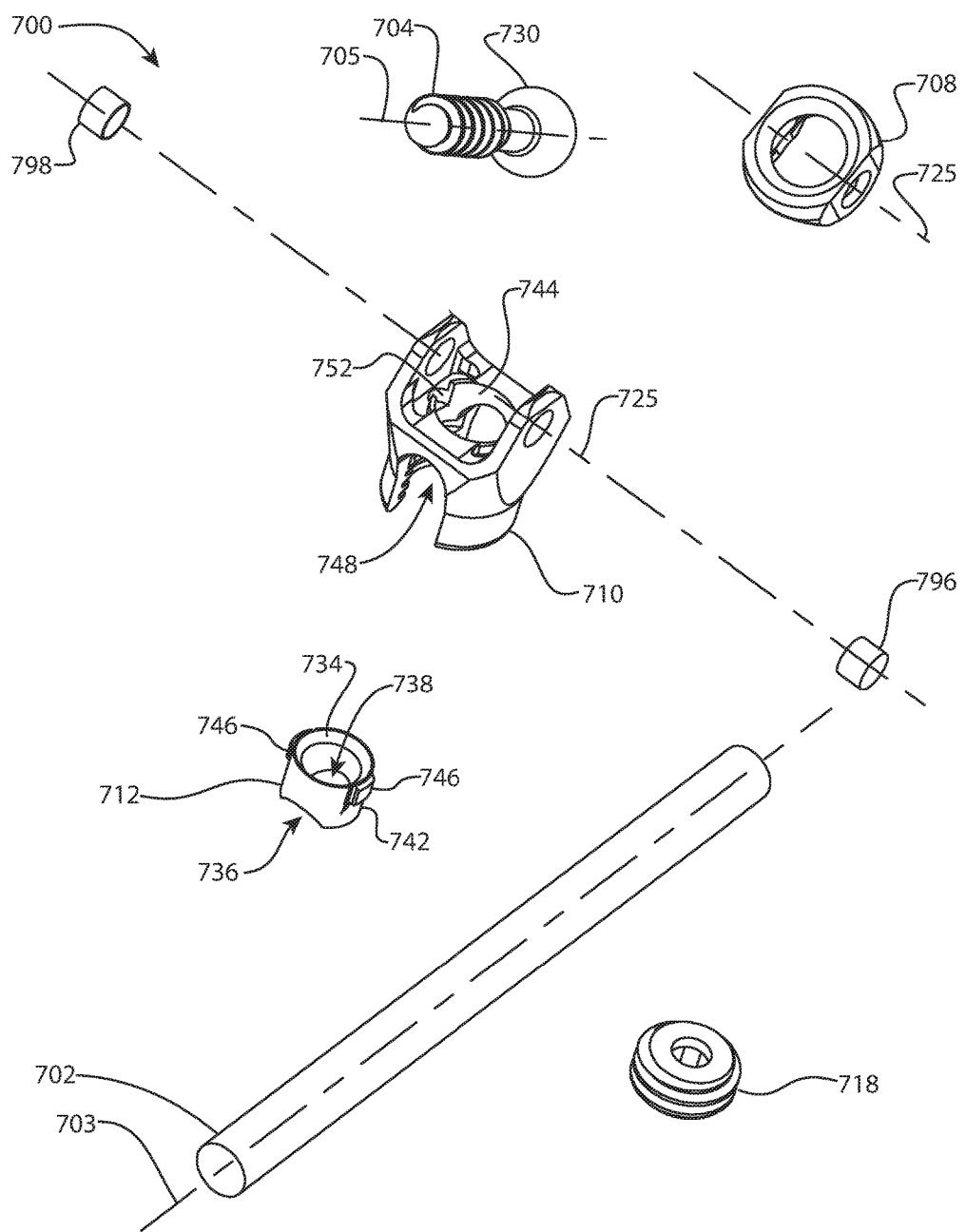
FIG. 28 is another exploded view of the screw and rod system of FIG. 22 from another viewpoint.

Referring to FIGS. 22-28, yet another screw and rod system 700 includes a rod 702, a screw 704, a carrier 708, a body 710, a lower saddle 712, and a locking element 718. The rod 702 has a central longitudinal axis 703. The screw 704 has a central longitudinal axis 705.

The screw 704 and the carrier 708 form a first joint 720. The first joint 720 may be a ball and socket joint, or a modification thereof, which permits multidirectional or polyaxial rotation of the screw 704 relative to the carrier 708 about a pivot point 721, seen best in FIG. 25. The range of motion of the screw axis 705 relative to the carrier 708 is a cone having its apex coincident with the point 721. The cone may have an included angle of at least 55 degrees, at least 57 degrees, at least 59 degrees, at least 60 degrees, at least 61 degrees, at least 63 degrees, or at least 65 degrees. The first joint 720 may alternately be a hinge joint or another type of joint. The first joint 720 may be formed between a head 730 of the screw 704 and a socket 732 of the carrier 708. The head 730 of the screw 704 and the socket 732 of the carrier 708 may include complementary convex and concave spherical portions which form the first joint 720, as seen best in FIGS. 25-28. The concave spherical portion may instead be a conical socket. The point 721 may be centered in the convex spherical head 730 of the screw 704.

The lower saddle 712 and the head 730 of the screw 704 may form a joint 722. The joint 722 may be a ball and socket joint, or a modification thereof, which permits multidirectional or polyaxial rotation about a point, as illustrated. In this example, the joint 722 permits rotation about the same point 721 as the first joint 720. The joint 722 may be concentric with the first joint 720. The joint 722 may alternately be a hinge joint or another type of joint. The joint 722 may be formed between the head 730 of the screw 704 and a socket 734 of the lower saddle 712. The head 730 of the screw 704 and the socket 734 of the lower saddle 712 may include complementary convex spherical portions which form the joint 722. The concave spherical portion may instead be a conical socket.

The rod 702 rests in a groove 736 of the lower saddle 712. The rod 702 and the lower saddle 712 may have complementary convex and concave cylindrical portions where they make contact. The concave cylindrical portion may instead be a V-groove.

Referring to FIGS. 25-28, the lower saddle 712 is pierced by an opening or hole 738. When the screw 704 and the lower saddle 712 are aligned, the opening 738 provides access for a driver to be inserted into a drive feature 740 of the head 730 of the screw 704 to drive the screw 704 into bone before the rod 702 is installed. The lower saddle 712 includes a cylindrical portion 742 which fits into a cylindrical socket 744 in the body 710 so that the lower saddle 712 is free to translate along the cylindrical socket 744. The lower saddle 712 includes bilateral projections 746 that rest in bilateral grooves 752 of the body 710 so that the lower saddle 712 is prevented from rotating relative to the body 710. The body 710 includes a slot 748 that receives the rod 702.

The carrier 708 and the body 710 form a second joint 724; one or more pins 796, 798 may also be included in the second joint. The second joint 724 may be a hinge joint, or a modification thereof, which permits rotation about an axis 725. Axis 725 is seen best in FIG. 26. The second joint 724 may be located beside the first joint 720 and the joint 722, and the point 721 may lie on the axis 725. The range of motion of the carrier 708 relative to the body 710 may have an included angle of at least 35 degrees, at least 37 degrees, at least 39 degrees, at least 40 degrees, at least 41 degrees, at least 43 degrees, or at least 45 degrees. The combination of the first joint 720 and the joint 722 provides greater angular range of motion between the axis 705 of the screw 704 and the axis 703 of the rod 702 than does a design with only one joint. For example, a first joint 720 having a range of motion with an included angle of 60 degrees and a second joint 724 having a range of motion with an included angle of 40 degrees results in an effective angular range of motion between the screw axis 705 and the rod axis 703 having an included angle of 100 degrees, along the rod axis 703 (i.e., in a plane that includes the rod axis 703 and the pivot point 721 and is perpendicular to the axis 725). For at least this reason, the range of motion of the first joint 720 and the range of motion of the second joint 724 may be called additive because they add together along the rod. The range of motion of the first joint 720 and the range of motion of the second joint 724 may also be called independent, since motion can occur at the first joint 720 without any motion at the second joint 724, and vice versa.

The locking element 718 may be a threaded fastener, or it may include a quarter turn locking mechanism, bayonet connection, or other locking mechanism. The locking element 718 engages the body 710, to provide a compressive force against the rod 702, the lower saddle 712, and the screw 704 within the carrier 708.

The sub-assembly of the carrier 708 and the body 710 may be referred to as a tulip sub-assembly. The tulip sub-assembly may also include the locking element 718, lower saddle 712, screw 704, pin 796, and/or pin 798.

A method of using the screw and rod system 700 may include the following steps: inserting the screw 704 into the carrier 708 to form the first joint 720; hinging the carrier 708 to the body 710; inserting the lower saddle 712 into the body 710 to form the joint 722, the lower saddle 712 resting on the head 730 of the screw 704; inserting a driver through the opening piercing the lower saddle 712 and into engagement with the drive feature 740 of the head 730 of the screw 704; inserting the screw 704 into bone, the screw 704 carrying the carrier 708, the body 710, and the lower saddle 712; removing the driver; rotating the carrier 708 and/or the body 710 to align the slot 748 of the body 710 with the axis of the rod 702 and to orient the axis 725 transverse to the rod 702; inserting the rod 702 into the slot 748 of the body 710 to rest on the lower saddle 712; inserting the locking element 718 into the body 710 to rest on the rod 702; partially tightening the locking element 718 to produce a first resistance in the system 700; repositioning the rod 702 relative to the screw 704 by polyaxial rotation of the first joint 720 and/or the joint 722 about the point 721, and/or by rotation of the second joint 724 about the axis 725; and fully tightening the locking element 718 to produce a second resistance in the system 700, wherein the second resistance is greater than the first resistance, wherein the second resistance locks the rod 702, the screw 704, the carrier 708, the body 710, the lower saddle 712, the cap 716, and the locking element 718 together.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim in this application, or any application claiming priority to this application, requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

The invention claimed is:

1. A screw and rod system comprising:
   a screw with a spherical head, a shaft extending from the spherical head, and a central longitudinal screw axis extending along the shaft;
   a rod with a central longitudinal rod axis extending along the rod; and
   a tulip sub-assembly comprising a carrier and a body, wherein the carrier comprises a carrier socket that receives the spherical head of the screw, wherein the body comprises a slot that receives the rod;
   wherein the carrier forms a hinge joint with the body so that the carrier has a first range of motion relative to the body about a hinge axis, wherein, when the slot of the body receives the rod, the hinge axis is transverse to the rod axis;
   wherein the spherical head of the screw forms a ball and socket joint with the carrier socket so that the screw has a second range of motion relative to the carrier about a pivot point centered in the spherical head of the screw, wherein the second range of motion is a cone, wherein the pivot point lies on the hinge axis;
   wherein the first range of motion and the second range of motion are additive in a plane that includes the rod axis and the pivot point, wherein the plane is perpendicular to the hinge axis.

2. The screw and rod system of claim 1, wherein the first range of motion has an included angle of at least 35 degrees and the second range of motion has an included angle of at least 55 degrees.

3. The screw and rod system of claim 1, wherein the tulip sub-assembly further comprises a lower saddle component, wherein the lower saddle component comprises a saddle socket that receives the spherical head of the screw, wherein the spherical head of the screw forms a joint with the saddle socket.

4. The screw and rod system of claim 3, wherein a socket of the body receives a portion of the lower saddle component, wherein the lower saddle component is free to translate along the socket of the body, wherein the lower saddle component is prevented from rotating relative to the body.

5. The screw and rod system of claim 4, wherein a groove of the lower saddle component receives the rod, wherein the groove is opposite the saddle socket.

6. The screw and rod system of claim 5, wherein the tulip sub-assembly comprises a locking element that engages the body to apply a compressive force against the rod, the lower saddle, and the screw within the carrier.

7. The screw and rod system of claim 1, wherein the body comprises a cylindrical socket that comprises a central longitudinal socket axis, wherein when the carrier and the body are coupled together to form the hinge joint, the hinge axis is transverse to the socket axis.

8. A screw and rod system comprising:
   a screw with a spherical head, a shaft extending from the spherical head, and a central longitudinal screw axis extending along the shaft; and
   a rod with a central longitudinal rod axis extending along the rod;
   wherein the screw has a first range of motion relative to the rod about a hinge axis, wherein the hinge axis is transverse to the rod axis;
   wherein the screw has a second range of motion relative to the rod about a pivot point centered in the spherical head, wherein the second range of motion is a cone, wherein the pivot point lies on the hinge axis;
   wherein the first and second ranges of motion are additive about the hinge axis so that the screw has an effective range of motion about the hinge axis that is greater than the second range of motion, wherein the effective range of motion is in a plane that includes the rod axis and the pivot point, wherein the plane is perpendicular to the hinge axis.

9. The screw and rod system of claim 8, wherein the first range of motion has an included angle of at least 35 degrees, the second range of motion has an included angle of at least 55 degrees, and the effective range of motion has an included angle of at least 90 degrees.

10. The screw and rod system of claim 8, comprising a carrier coupled by a first ball and socket joint to the spherical head of the screw, wherein the screw rotates relative to the carrier about the pivot point, wherein the carrier is coupled by a hinge joint to a body component, wherein the carrier rotates relative to the body component about the hinge axis, wherein the body component comprises a slot that receives the rod.

11. The screw and rod system of claim 10, comprising a lower saddle component coupled by a second ball and socket joint to the spherical head of the screw, wherein the screw rotates relative to the lower saddle component about the pivot point, wherein the lower saddle component comprises a groove that receives the rod, wherein the groove is opposite the second ball and socket joint.

12. The screw and rod system of claim 11, wherein a cylindrical portion of the lower saddle component is received in a cylindrical socket of the body component, wherein the lower saddle component is free to translate along the cylindrical socket of the body component, wherein the lower saddle component is prevented from rotating within the cylindrical socket of the body component.

13. The screw and rod system of claim 12, wherein the cylindrical socket of the body component comprises a central longitudinal socket axis, wherein the hinge joint comprises the hinge axis, wherein when the carrier and the body component are coupled together by the hinge joint, the hinge axis is transverse to the socket axis.

14. The screw and rod system of claim 11, comprising a locking element that engages the body component to apply a compressive force against the rod, the lower saddle component, and the screw within the carrier.

15. A screw and rod system comprising:
- a screw with a spherical head, a shaft extending from the spherical head, a pivot point centered in the spherical head, and a central longitudinal screw axis extending along the shaft; and
- a rod with a central longitudinal rod axis extending along the rod;
- wherein the screw has a first range of motion relative to the rod about a hinge axis, wherein the hinge axis is transverse to the rod axis;
- wherein the screw has a second range of motion relative to the rod about the pivot point, wherein the second range of motion is a cone, wherein the pivot point lies on the hinge axis;
- wherein the second range of motion is independent of the first range of motion;
- wherein the first range of motion and the second range of motion are additive in a plane that includes the rod axis and the pivot point, wherein the plane is perpendicular to the hinge axis.

16. The screw and rod system of claim 15, wherein the first range of motion has an included angle of at least 35 degrees and the second range of motion has an included angle of at least 55 degrees.

17. The screw and rod system of claim 15, comprising a carrier coupled by a first ball and socket joint to the spherical head of the screw, wherein the screw rotates relative to the carrier about the pivot point, wherein the carrier is coupled by a hinge joint to a body component, wherein the carrier rotates relative to the body component about the hinge axis, wherein the body component comprises a slot that receives the rod.

18. The screw and rod system of claim 17, comprising a lower saddle component coupled by a second ball and socket joint to the spherical head of the screw, wherein the screw rotates relative to the lower saddle component about the pivot point, wherein the lower saddle component comprises a groove that receives the rod, wherein the groove is opposite the second ball and socket joint, wherein a cylindrical portion of the lower saddle component is received in a socket of the body component, wherein the lower saddle component is free to translate along the socket of the body component, wherein the lower saddle component is prevented from rotating within the socket of the body component.

19. The screw and rod system of claim 18, comprising a locking element that engages the body component to apply a compressive force against the rod, the lower saddle component, and the screw within the carrier.

20. The screw and rod system of claim 18, wherein the socket of the body component is cylindrical and comprises a central longitudinal socket axis, wherein the hinge joint comprises the hinge axis, wherein when the carrier and the body component are coupled together by the hinge joint, the hinge axis is transverse to the socket axis.

* * * * *